United States Patent [19]
Nakagawa et al.

[11] Patent Number: 5,869,702
[45] Date of Patent: Feb. 9, 1999

[54] POLYOL ETHER DERIVATIVES AND PRODUCTION METHODS THEREFOR

[75] Inventors: Shoji Nakagawa; Hiroki Sawada; Hiroyasu Togashi; Toshiya Hagihara, all of Wakayama, Japan

[73] Assignee: Kao Corporation, Tokyo, Japan

[21] Appl. No.: 869,141

[22] Filed: Jun. 4, 1997

Related U.S. Application Data

[62] Division of Ser. No. 512,651, Aug. 8, 1995, Pat. No. 5,720,895.

[30] Foreign Application Priority Data

Aug. 11, 1994 [JP] Japan ................................ 6-212174

[51] Int. Cl.$^6$ ..................... C07D 317/18; C07D 319/06; C07D 319/08; C07D 407/04; C07C 41/00
[52] U.S. Cl. ................. 549/364; 549/365; 549/370; 549/372; 549/448; 549/453; 568/672; 568/679
[58] Field of Search .................. 549/364, 365, 549/370, 372, 448, 453; 568/672, 679

[56] References Cited

U.S. PATENT DOCUMENTS

| | | | |
|---|---|---|---|
| 3,741,986 | 6/1973 | Hartmann | 549/372 |
| 5,523,010 | 6/1996 | Sorensen et al. | 508/307 |
| 5,575,944 | 11/1996 | Sawada et al. | 252/68 |

FOREIGN PATENT DOCUMENTS

| | | |
|---|---|---|
| 0019999A1 | 12/1980 | European Pat. Off. . |
| 0092998A1 | 11/1983 | European Pat. Off. . |
| 0460614A1 | 12/1991 | European Pat. Off. . |
| 0624563A1 | 11/1994 | European Pat. Off. . |
| 2303815 | 3/1976 | France . |
| 4124199A1 | 1/1993 | Germany . |
| 5-98275 | 4/1993 | Japan . |
| 6057243 | 3/1994 | Japan . |
| 2100256 | 12/1982 | United Kingdom . |
| WO93/24435A1 | 12/1993 | WIPO . |
| 9606839 | 3/1996 | WIPO . |

*Primary Examiner*—Ba K. Trinh
*Attorney, Agent, or Firm*—Birch, Stewart, Kolasch & Birch, LLP

[57] ABSTRACT

Polyol ether derivatives, a method for producing the polyol ether derivatives, and a working fluid composition for a refrigerating machine containing a hydrofluorocarbon and a refrigeration oil containing the polyol ether derivatives as a base oil.

2 Claims, No Drawings

POLYOL ETHER DERIVATIVES AND PRODUCTION METHODS THEREFOR

This application is a divisional of application Ser. No. 08/512,651 filed on Aug. 8, 1995, now U.S. Pat. No. 5,720,895, the entire contents of which are hereby incorporated by reference.

BACKGROUND OF THE INVENTION

1. Field of the Invention

The present invention relates to polyol ether derivatives which are useful as polar oils, organic solvents, lubricants, synthetic lubricating oils, or refrigeration oils, or as intermediates in the production of the above oils, etc.; and to a method for producing the polyol ether derivatives; and also to a working fluid composition for a refrigerating machine using the above polyol ether derivatives as a base oil. Here, the term "polyol ether" means a partially etherified polyol.

2. Discussion of the Related Art

Recently, the use of dichlorodifluoromethane (CFC12) for refrigerators and car air conditioners has been restricted, and will be legally banned in order to protect the ozone layer. Also, the use of chlorodifluoromethane (HCFC22) for room air conditioners is about to be legally regulated. Thus, hydrofluorocarbons which do not destroy the ozone layer, such as 1,1,1,2-tetrafluoroethane (HFC 134a), difluoromethane (HFC32), and pentafluoroethane (HFC125), have been developed as substitutes for CFC12 or HCFC22.

However, since the polarity of hydrofluorocarbons is higher than that of CFC12 or HCFC22, the use of conventional lubricating oils, such as naphthenic mineral oils, poly-α-olefins, or alkylbenzenes, causes two-layer separation of the working fluid at low temperatures. This is due to poor compatibility between the conventional lubricating oils and hydrofluorocarbons. Two-layer separation hampers oil return, which in turn interferes with heat transfer due to deposition of a thick oil film on a heat transfer surface of the condenser and evaporator used as heat exchangers. It can also cause significant failures, such as poor lubrication, and foaming upon starting operation. Therefore, the conventional refrigeration oils cannot be used as refrigeration oils under these new refrigerant atmospheres.

As for lubricity, CFC12 and HCFC22 generate hydrogen chloride upon partial decomposition. The hydrogen chloride thus formed reacts with the friction surface to form a coating of chlorides, thereby improving the lubricity. On the other hand, non chlorine containing hydrofluorocarbons are not expected to have such an effect; therefore, refrigeration oils used in combination with hydrofluorocarbons are required to have a further excellent lubricity when compared to the conventional refrigeration oils.

In addition, the refrigeration oils used in combination with hydrofluorocarbons have to have good thermal stability in the presence of hydrofluorocarbons.

Moreover, with compression-type refrigerating machines for electric refrigerators and air conditioners, since organic materials are used for motor components, such as insulators and enameled wires, the working fluid comprising a hydrofluorocarbon and a refrigeration oil is required to have no adverse effects on these organic materials and also have a good insulating property.

Refrigeration oils which can be used in combination with hydrofluorocarbons, such as 1,1,1,2-tetrafluoroethane (HFC134a), disclosed in U.S. Pat. No. 4,755,316 and Japanese Patent Laid-Open No. 2-129294, are ether compounds of polyalkylene glycols (hereinafter abbreviated as PAG-OH) prepared by the addition of an alkylene oxide to a polyhydric alcohol which is not alkyl-capped at the terminal hydroxyl. As an example of the polyhydric alcohols used, the former discloses trimethylol propane and the latter discloses glycerol.

In order to solve various problems of the above compounds, such as poor compatibility with HFC and high hygroscopicity, compounds prepared by alkyl-capping the terminal hydroxyl groups of the above ether compounds (hereinafter abbreviated as PAG) are disclosed in Japanese Patent Laid-Open Nos. 3-14894, 3-205492, 4-20596, 4-359996, and 5-98275.

Since PAG-OH and PAG have a higher polarity than the naphthenic mineral oils, their compatibility with HFC134a at low temperatures is good. However, PAG-OH and PAG phase-separate as the temperature increases as mentioned in U.S. Pat. No. 4,755,316. There are also several problems with these compounds. For example, a poor insulating property is one of the problems. Due to this significant problem, PAG-OH and PAG cannot be used for a refrigerating device of electric refrigerators and air conditioners where a motor is incorporated in a compressor. Therefore, applications of PAG-OH and PAG are proposed for car air conditioners where their poor insulating property does not cause any problems. High hygroscopicity is another significant problem of PAG-OH and PAG. The water absorbed by the compounds causes thermal instability of the compounds in the presence of HFC134a, and hydrolysis of organic materials, such as PET films.

In order to solve the above problems of polyether compounds, such as poor insulating property and high hygroscopicity, ester compounds and carbonate compounds have been developed. For example, mixed oils of polyether oils and ester oils are disclosed in U.S. Pat. No. 4,851,144 (corresponding to Japanese Patent Laid-Open No. 2-276894) and Japanese Patent Laid-Open No. 2-158693; ester oils are disclosed in Japanese Patent Laid-Open Nos. 3-505602, 3-128991, and 3-128992; and carbonate oils are disclosed in Japanese Patent Laid-Open Nos. 2-132178 and 3-149295, and European Patent No. 421,298. All of the compounds disclosed can be used as a refrigeration oil in combination with 1,1,1,2-tetrafluoroethane (HFC134a).

Ester compounds and carbonate compounds show good compatibility with hydrofluorocarbons and high thermal stability in the presence of hydrofluorocarbons. Also, these compounds have markedly better insulating properties and much lower hygroscopicity than polyether compounds.

However, when compared with the conventional CFC12-mineral oil working fluid system, both freon and oil tend to have a high polarity in the hydrofluorocarbon-ester oil system or hydrofluorocarbon-carbonate oil system, and the systems become highly hygroscopic. Particularly, in the system using an ester oil, a carboxylic acid is likely to be formed owing to hydrolysis of the ester oil, and the formed carboxylic acid may in turn corrode and wear down the metals. Also, in the case of using a carbonate oil, there arises such a problem that a non-condensable carbon dioxide gas is generated owing to hydrolysis of the carbonate oil to cause a low refrigerating capacity.

In particular, in the case of room air conditioners, it is common practice to fill an air conditioner with a refrigerant upon installation. Therefore, unlike refrigerating machines for which filling of refrigerant is carried out in a factory, it is almost impossible to prevent a working fluid of room air conditioners from being contaminated with water.

Therefore, there has been a concern about the reliability of the hydrofluorocarbon-ester oil system and hydrofluorocarbon-carbonate oil system, when used in room air conditioners.

WO93/24435 discloses that a polyvinyl ether compound having good compatibility with hydrofluorocarbons and good insulating property is prepared by polymerization of vinyl ether monomers and subsequent hydrogenation. However, since the polyvinyl ether compound is synthesized by polymerization, it shows molecular weight distribution. Therefore, a part of high molecular weight polymers sometimes causes plugged capillaries of refrigerating machines and worsens the compatibility of the compound with hydrofluorocarbons. Also, the compound requires complicated post-treatment and cannot always be obtained in high yield because the vinyl ether monomers, the starting materials of the polyvinyl ether compound, are not stable substances. In particular, the yield of those with a low degree of polymerization (around 6) is low. Some vinyl ether monomers of certain structures cannot be easily obtained, and are, therefore, very expensive.

As mentioned above, polyvinyl ether compounds show molecular weight distribution. The products with higher molecular weights sometimes cause to impair the performance of the compounds. Polyvinyl ether compounds also have drawbacks of limited availability of the starting materials and poor yields of those with low degrees of polymerization, which together make the product cost expensive.

The refrigerant-oil systems developed so far have various drawbacks as mentioned above. The hydrofluorocarbon-PAG (PAG-OH) oil system has problems in hygroscopicity and insulating property; and the hydrofluorocarbon-ester oil system and the hydrofluorocarbon-carbonate oil system have problems of poor hydrolysis resistance. Both of these systems are unsatisfactory as a working fluid composition for a refrigerating machine, because, as compared with the conventional CFC12-mineral oil system, they have higher hygroscopicity, lower thermal stability, stronger deteriorating action on organic materials, and stronger effects to corrode and wear metals. Polyvinyl ether compounds show a molecular weight distribution and the molecules with high molecular weights cause to lower the compatibility with hydrofluorocarbons. Polyvinyl ether compounds also have drawbacks of limited availability of the starting materials and of high cost.

SUMMARY OF THE INVENTION

Accordingly, it is an object of the present invention to provide novel polyol ether derivatives that can make an inexpensive base oil for a working fluid composition for a refrigerating machine, the novel polyol ether derivatives having excellent compatibility with hydrofluorocarbons, high thermal stability, strong resistance against hydrolysis, appropriate kinematic viscosity, good fluidity at low temperatures, and especially good volume resistivity, thereby solving the above problems.

It is another object of the present invention to provide a method by which the above polyol ether derivatives are industrially advantageously produced.

It is still another object of the present invention to provide a working fluid composition for a refrigerating machine comprising a refrigeration oil containing, as a base oil, the polyol ether derivatives and a hydrofluorocarbon.

Known polyol ether derivatives each having an alcohol residue from a hexahydric alcohol, such as sorbitol and mannitol are hexamethyl ether, hexavinyl ether, hexaoleyl ether, 1,3,4,5,6-pentamethyl ether (monool), 2,3,4,5,6-pentabenzyl ether (monool), 1,3,5-trimethyl-6-triphenyl methyl ether (diol), 1,2,5,6-tetrakistetradecyl ether (diol), 1,4,5-triethyl ether (trial), 2,3,5-trisdodecyl ether (triol), 1,6-didodecyl ether (tetraol), 2,5-dibenzyl ether (tetraol), 1-t-butyl ether (pentaol), and 1-hexadecyl ether (pentaol).

However, polyol ether derivatives having an ether alkyl group (an alkyl group bound to an oxygen atom) which is branched at α-position, i.e. polyol ether derivatives having secondary or tertiary alkyl groups as an ether alkyl group; and polyol ether derivatives having branched ether alkyl groups of 3 to 17 carbon atoms have yet to be known except for those having t-butyl groups as ether alkyl groups.

As a result of intense research in view of the above objects, the present inventors have found that polyol ether derivatives having a certain structure and not having an alkylene oxide group in a molecule can achieve the above objects.

For producing such polyol ether derivatives, there have been methods in which a hexahydric alcohol reacts with an alkylating agent, such as a dialkyl sulfate, an alkyl tosylate, and an alkyl halide. The methods however have a problem that the desired product cannot be obtained in a high yield except when the alkyl of alkylating agent is a primary alkyl, and a problem that by-products such as sulfates and common salt are produced in high amounts, especially when the degree of etherification is increased, causing disadvantages in terms of production and economy.

In this situation, the present inventors have found that the polyol ether derivatives of the present invention can easily be obtained by carrying out a reaction of a hexahydric alcohol with a carbonyl compound to form an intermediate cyclic acetal, and hydrogenating or hydrogenating and alkyl-capping the cyclic acetal to give the polyol ether derivatives.

The present invention has been achieved based upon the above findings.

In brief, the present invention is directed to:

(1) A polyol ether derivative represented by any one of the following general formulas (I) to (IV):

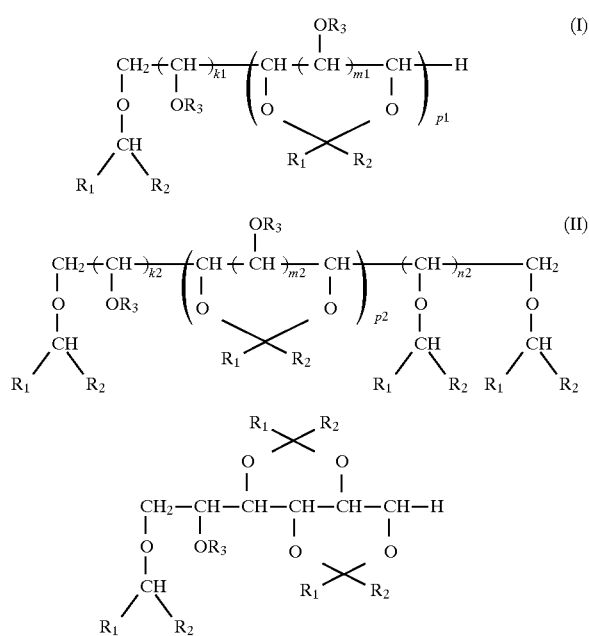

-continued

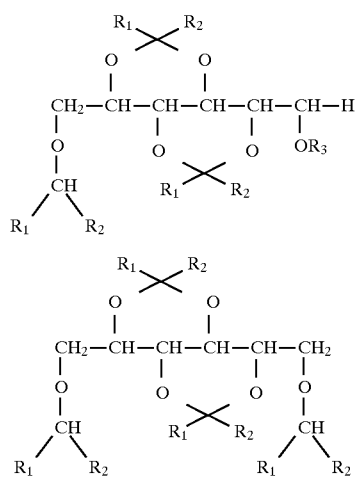

wherein $R_1$ represents a hydrogen atom, a linear alkyl group having 1–21 carbon atoms or a branched alkyl group having 3–21 carbon atoms; $R_2$ represents a branched alkyl group having 3–17 carbon atoms when $R_1$ represents a hydrogen atom, or $R_2$ represents a linear alkyl group having 1–21 carbon atoms or a branched alkyl group having 3–21 carbon atoms when $R_1$ represents a linear alkyl group having 1–21 carbon atoms or a branched alkyl group having 3–21 carbon atoms; $R_1$ and $R_2$ may together join to form a ring with an alkylene group having 2–13 carbon atoms; 2 to 6 pairs of $R_1$ and $R_2$ may be identical or different; $k_1$ represents a number of 0–5, $p_1$ represents a number of 0–2, $m_1$ represents 0 or 1, wherein $k_1$, $p_1$ and $m_1$ satisfy the equation $k_1+(m_1+2)p_1=5$; $k_2$ and $n_2$ each represents a number of 0–4, $p_2$ represents a number of 0–2, $m_2$ represents 0 or 1, wherein $k_2$, $p_2$, $m_2$ and $n_2$ satisfy the equation $k_2+(m_2+2)p_2+n_2=4$; $R_3$ represents a hydrogen atom, a linear alkyl group having 1–8 carbon atoms or a branched alkyl group having 3–8 carbon atoms; and repeating units in formulas (I) and (II), namely methylene groups substituted with oxygen-containing group (hereinafter, simply referred to as O-methylene groups) in the number of $k_1$ and cyclic acetal (or ketal) units in the number of $p_1$ in formula (I), and O-methylene groups in the numbers of $k_2$ and $n_2$ and cyclic acetal (or ketal) units in the number of $p_2$ in formula (II) may be arranged at random or in block form;

(2) The polyol ether derivative described in (1) above, wherein an alcohol residue of the polyol ether derivative is derived from sorbitol;

(3) A method for producing a polyol ether derivative represented by any one of formulas (VII) to (X), comprising the steps of:

reacting a hexahydric alcohol represented by the following formula (V):

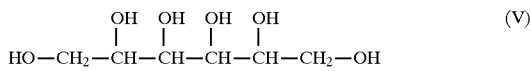

with a carbonyl compound represented by the following formula (VI):

wherein $R_1$ represents a hydrogen atom, a linear alkyl group having 1–21 carbon atoms or a branched alkyl group having 3–21 carbon atoms; and $R_2$ represents a linear alkyl group having 1–21 carbon atoms or a branched alkyl group having 3–21 carbon atoms, or with a reactive derivative thereof, i.e., an acetal or a ketal, in the presence of an acid catalyst to form a cyclic acetal or a cyclic ketal; and hydrogenating, and optionally further alkylating the cyclic acetal or the cyclic ketal to give a polyol ether derivative represented by the following formulas (VII) to (X):

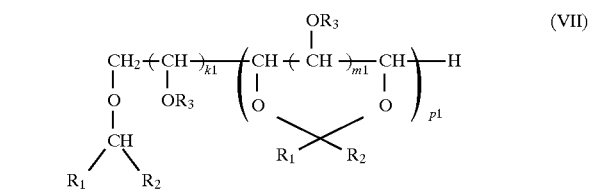

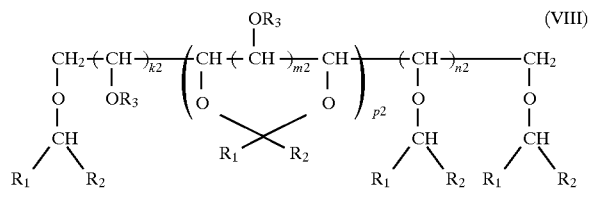

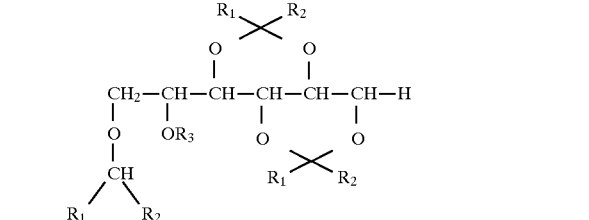

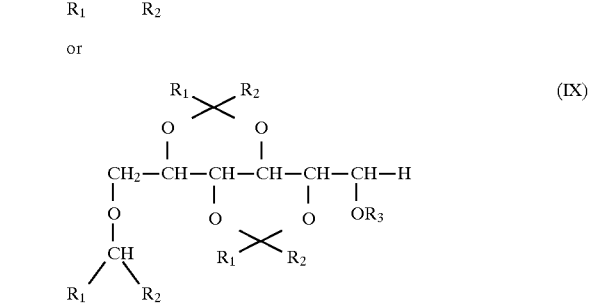

wherein $R_1$ represents a hydrogen atom, a linear alkyl group having 1–21 carbon atoms or a branched alkyl group having 3–21 carbon atoms; $R_2$ represents a linear alkyl group having 1–21 carbon atoms or a branched alkyl group having 3–21 carbon atoms; $R_1$ and $R_2$ may together join to form a ring with an alkylene group having 2–13 carbon atoms; 2 to 6 pairs of $R_1$ and $R_2$ may be identical or different; $k_1$ represents a number of 0–5, $p_1$ represents a number of 0–2, $m_1$ represents 0 or 1, wherein $k_1$, $p_1$ and $m_1$ satisfy the equation $k_1+(m_1+2)p_1=5$; $k_2$ and $n_2$ each represents a number of 0–4, $p_2$ represents a number of 0–2, $m_2$ represents 0 or 1, wherein $k_2$, $p_2$, $m_2$ and $n_2$ satisfy the equation $k_2+(m_2+2)p_2+n_2=4$; $R_3$ represents a hydrogen atom, a linear alkyl group having 1–8 carbon atoms or a branched alkyl group having 3–8 carbon atoms; and repeating units in formulas (VII) and (VIII), namely O-methylene groups in the number of $k_1$ and cyclic acetal (or ketal) units in the number of $p_1$ in formula (VII), and O-methylene groups in the number of $k_2$ and $n_2$ and cyclic acetal (or ketal) units in the number of $p_2$ in formula (VIII) may be arranged at random or in block form;

(4) The method described in (3) above, wherein the hexahydric alcohol represented by formula (V) is sorbitol;

(5) The method described in (3) or (4) above, wherein, in formulas (VII) to (X), $R_1$ represents a hydrogen atom and $R_2$ represents a linear alkyl group having 1–13 carbon atoms or a branched alkyl group having 3–13 carbon atoms, or wherein $R_1$ and $R_2$ in formulas (VII) to (X) each represents a linear alkyl group having 1–13 carbon atoms or a branched alkyl group having 3–13 carbon atoms;

(6) A working fluid composition for a refrigerating machine, comprising a hydrofluorocarbon and a refrigeration oil containing a polyol ether derivative represented by the following formula (XI) as a base oil:

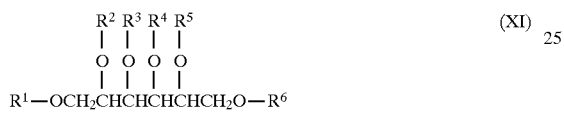

wherein $R^1$ to $R^6$ may be identical or different, each representing a linear alkyl group having 1–14 carbon atoms, a branched alkyl group having 3–14 carbon atoms or a cyclic alkyl group having 3–14 carbon atoms and the total number of carbon atoms of $R^1$ to $R^6$ being 8 to 40;

(7) The working fluid composition for a refrigerating machine described in (6) above, wherein a hexahydric alcohol residue of the compound represented by formula (XI) is derived from sorbitol;

(8) The working fluid composition for a refrigerating machine described in (6) or (7) above, wherein the compound represented by formula (XI) is synthesized by the steps of:

reacting a hexahydric alcohol represented by the following formula (V):

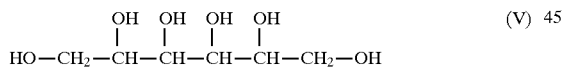

with (a) one or more carbonyl compounds represented by the following formula (XII) for ketalization or acetalization:

wherein $R^7$ represents a hydrogen atom, a linear alkyl group having 1–13 carbon atoms, a branched alkyl group having 3–13 carbon atoms or a cyclic alkyl group having 3–13 carbon atoms, and $R^8$ represents a linear alkyl group having 1–13 carbon atoms, a branched alkyl group having 3–13 carbon atoms or a cyclic alkyl group having 3–13 carbon atoms with the proviso that $R^7$ and/or $R^8$ have at least one hydrogen atom at α-position to the carbonyl group, and the total number of carbon atoms of $R^7$ and $R^8$ is 1–13; and $R^7$ and $R^8$ may together join to form a ring with an alkylene group having 2–13 carbon atoms, or with (b) reactive derivatives of the carbonyl compounds (ketal or acetal) for transketalization or transacetalization to obtain a cyclic ketal or a cyclic acetal;

hydrogenating the cyclic ketal or the cyclic acetal to obtain a polyol ether; and alkylating the polyol ether to give a polyol ether derivative;

(9) The working fluid composition for a refrigerating machine described in (6) or (7) above, which further comprises one or more compounds selected from the group consisting of (a) 0.05 to 2.0 parts by weight of an epoxy compound, (b) 0.01 to 100 parts by weight of an orthoester compound, (c) 0.01 to 100 parts by weight of acetal or ketal, and (d) 0.05 to 5 parts by weight of carbodiimide, each amount of (a) to (d) being based on 100 parts by weight of the polyol ether derivative represented by formula (XI);

(10) The working fluid composition for a refrigerating machine described in (8) above, which further comprises one or more compounds selected from the group consisting of (a) 0.05 to 2.0 parts by weight of an epoxy compound, (b) 0.01 to 100 parts by weight of an orthoester compound, (c) 0.01 to 100 parts by weight of acetal or ketal, and (d) 0.05 to 5 parts by weight of carbodiimide, each amount of (a) to (d) being based on 100 parts by weight of the polyol ether derivative represented by formula (XI);

(11) A working fluid composition for a refrigerating machine, comprising a hydrofluorocarbon and a refrigeration oil containing as a base oil a polyol ether derivative represented by the following formula $(XIII_{AA})$ or $(XIII_{BB})$:

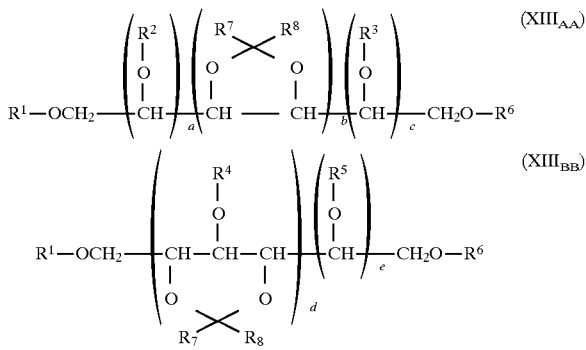

wherein $R^1$ to $R^6$ may be identical or different, each representing a linear alkyl group having 1–14 carbon atoms, a branched alkyl group having 3–14 carbon atoms or a cyclic alkyl group having 3–14 carbon atoms; $R^7$ represents an hydrogen atom, or a linear alkyl group having 1–13 carbon atoms, a branched alkyl group having 3–13 carbon atoms or a cyclic alkyl group having 3–13 carbon atoms; $R^8$ represents a linear alkyl group having 1–13 carbon atoms, a branched alkyl group having 3–13 carbon atoms or a cyclic alkyl group having 3–13 carbon atoms; $R^7$ and $R^8$ may together join to form a ring with an alkylene group having 2–13 carbon atoms; the total number of carbon atoms is 8–40 for $R^1$, $R^2$, $R^3$, $R^6$, $R^7$ and $R^8$ in formula $(XIII_{AA})$, and for $R^1$, $R^4$, $R^5$, $R^6$, $R^7$ and $R^8$ in formula $(XIII_{BB})$, and is 1–13 for $R^7$ and $R^8$ in formulas ($XIII_{AA}$ and $XIII_{BB}$); and "a" to "e" are symbols for structure unit, and may be arranged in any sequential order;

(12) The working fluid composition for a refrigerating machine described in (11) above, wherein a hexahydric alcohol residue of the compound represented by formula $(XIII_{AA})$ or $(XIII_{BB})$ is derived from sorbitol;

(13) The working fluid composition for a refrigerating machine described in (11) or (12) above, wherein the compound represented by formula ($XIII_{AA}$) or ($XIII_{BB}$) is synthesized by the steps of:

reacting a hexahydric alcohol represented by the following formula (V):

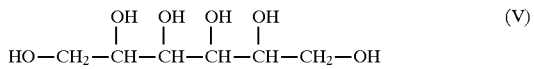

with (a) one or more carbonyl compounds represented by the following formula (XII) for ketalization or acetalization:

wherein $R^7$ represents a hydrogen atom, a linear alkyl group having 1–13 carbon atoms, a branched alkyl group having 3–13 carbon atoms or a cyclic alkyl group having 3–13 carbon atoms, and $R^8$ represents a linear alkyl group having 1–13 carbon atoms, a branched alkyl group having 3–13 carbon atoms, or a cyclic alkyl group having 3–13 carbon atoms with the proviso that $R^7$ and/or $R^8$ have at least one hydrogen atom at α-position to the carbonyl group, and the total number of carbon atoms of $R^7$ and $R^8$ is 1–13; and $R^7$ and $R^8$ may together join to form a ring with an alkylene group having 2–13 carbon atoms; or with (b) reactive derivatives of the carbonyl compounds (ketal or acetal) thereof for transketalization or transacetalization to obtain a cyclic ketal or a cyclic acetal;
hydrogenating the cyclic ketal or the cyclic acetal to obtain a polyol ether ketal or a polyol ether acetal; and
alkylating the polyol ether ketal or the polyol ether acetal;

(14) The working fluid composition for a refrigerating machine described in (11) or (12) above, which further comprises one or more compounds selected from the group consisting of (a) 0.05 to 2.0 parts by weight of an epoxy compound, (b) 0.01 to 100 parts by weight of an orthoester compound, (c) 0.01 to 100 parts by weight of an acetal or a ketal, and (d) 0.05 to 5 parts by weight of carbodiimide, each amount of (a) to (d) being based on 100 parts by weight of the polyol ether derivative represented by formula ($XIII_{AA}$) or ($XIII_{BB}$);

(15) The working fluid composition for a refrigerating machine described in (13) above, which further comprises one or more compounds selected from the group consisting of (a) 0.05 to 2.0 parts by weight of an epoxy compound, (b) 0.01 to 100 parts by weight of an orthoester compound, (c) 0.01 to 100 parts by weight of an acetal or a ketal, and (d) 0.05 to 5 parts by weight of carbodiimide, each amount of (a) to (d) being based on 100 parts by weight of the polyol ether derivative represented by formula ($XIII_{AA}$) or ($XIII_{BB}$);

(16) The working fluid composition for a refrigerating machine described in (6) or (11) above, wherein the polyol ether derivative has an average molecular weight in the range of from 200 to 800;

(17) The working fluid composition for a refrigerating machine described in (6) or (11) above, wherein the polyol ether derivative has an average molecular weight in the range of from 300 to 700;

(18) The working fluid composition for a refrigerating machine described in (6) or (11) above, wherein the polyol ether derivative has a viscosity at 100° C. of from 0.5 to 30 mm²/s; and

(19) The working fluid composition for a refrigerating machine described in (6) or (11) above, wherein the polyol ether derivative has a viscosity at 40° C. of from 1 to 300 mm²/s.

According to the present invention, novel and useful polyol ether derivatives usable for preparation of synthetic lubricating oils and other various purposes can be produced from inexpensive starting materials by simple process.

A working fluid composition for a refrigerating machine comprising a hydrofluorocarbon and a refrigeration oil containing as a base oil novel polyol ether derivative of the present invention has the following excellent properties: good compatibility, good thermal stability, high hydrolysis resistance, adequate kinematic viscosity, good fluidity at low temperatures, and noticeably high volume resistivity. Thus, a working fluid composition for a refrigerating machine of the present invention can suitably be used for motor-integrated compression refrigerating machines used for refrigerators and room air conditioners.

DETAILED DESCRIPTION OF THE INVENTION

Here, for the sake of convenience, the present invention will be described in more detail according to the following three parts: (1) Novel polyol ether derivatives; (2) A novel method for producing polyol ether derivatives; and (3) A working fluid composition for a refrigerating machine comprising a refrigeration oil containing as a base oil polyol ether derivatives and a hydrofluorocarbon. In the present specification, substituent groups in the formulas are defined for each formula. Therefore, it should be noted that the definition for $R_2$, for example, is different between formulas (I)–(IV) and formulas (VI)–(X) and that it is interpreted differently between these two groups of formulas. Also, it should be noted that superior figures (e.g., $R^2$) in formulas (XI), ($XIII_{AA}$) and ($XIII_{BB}$) are used to clearly indicate that these substituents are defined differently from those in the other formulas (i.e., formulas (I) to (IV) and (VI) to (X)) where inferior figures (e.g., $R_2$) are used.

(1) Novel polyol ether derivatives

The novel polyol ether derivatives of the present invention are represented by any one of formulas (I) to (IV).

In formulas (I) to (IV), $R_1$ represents a hydrogen atom, a linear alkyl group having 1–21 carbon atoms or a branched alkyl group having 3–21 carbon atoms. Examples of the linear alkyl groups having 1–21 carbon atoms include methyl, ethyl, propyl, butyl, pentyl, hexyl, heptyl, octyl, nonyl, undecyl, tridecyl, pentadecyl, heptadecyl, nonadecyl, and heneicosyl; and examples of branched alkyls having 3–21 carbon atoms include 1-methyloctadecyl, 1-decylundecyl, and 2-methyleicosyl in addition to the branched alkyls having 3–17 carbon atoms exemplified below.

In formulas (I) to (IV), when $R_1$ represents a hydrogen atom, $R_2$ represents a branched alkyl having 3–17 carbon atoms, preferably 3–12 carbon atoms. Branched alkyls having 3–17 carbon atoms represented by $R_2$ are exemplified below.

Examples of α-methyl-branched alkyls include isopropyl, 1-methylpropyl, 1-methylbutyl, 1-methylpentyl, 1-methylhexyl, 1-methylheptyl, 1-methyloctyl, 1-methylnonyl, 1-methyldecyl, 1-methylundecyl, and 1-methylhexadecyl.

Examples of other α-branched alkyls include 1-ethylpropyl, 1-ethylbutyl, 1-ethylpentyl, 1-propylbutyl, 1-ethylhexyl, 1-propylpentyl, 1-ethylheptyl, 1-propylhexyl, 1-butylpentyl, 1-pentylhexyl, 1-hexylheptyl, 1-octylnonyl, and 1-hexylundecyl. Examples of cyclic alkyls branched at α-position include cyclopentyl, cyclohexyl, 3-(2',2',5'-trimethylcyclohexyl)propyl, and 1-cyclohexylmethyl.

Examples of α- and other polybranched alkyls having one or more branches at positions other than α-position include 1,2-dimethylpropyl, 1,2-dimethylbutyl, 1,3-dimethylbutyl, 1-ethyl-2-methylpropyl, diisopropylmethyl, 1,4-dimethylpentyl, 1-isopropylbutyl, 1,3,3-trimethylbutyl, 1,5-dimethylhexyl, 1-ethyl-2-methylpentyl, 1-butyl-2-methylpropyl, 1-ethyl-3-methylpentyl, diisobutylmethyl, and 1,5,9-trimethyldecyl.

Examples of β-branched alkyls include 2-methylpropyl, 2-methylbutyl, 2-methylpentyl, 2-ethylbutyl, 2-methylhexyl, 2-ethylpentyl, 2-methylheptyl, 2-ethylhexyl, and 2-propylpentyl.

Examples of β- and other polybranched alkyls having one or more branches at positions other than α- and β-positions include 2,3-dimethylbutyl, 2,4,4-trimethylpentyl, and 2-isopropyl-5-methylhexyl.

Examples of other branched alkyls having one or more branches at positions other than α- and β-positions include 3-methylbutyl, 3-methylpentyl, 4-methylpentyl, 3,3-dimethylbutyl, 3-methylhexyl, 4-methylhexyl, 5-methylhexyl, 3,5,5-trimethylhexyl, isodecyl, 3,7-dimethyloctyl, and isoheptadecyl.

Examples of alkyls having a tertiary carbon with no hydrogen atom at β-position include 2,2-dimethylpropyl, 2,2-dimethylbutyl, 2,2-dimethylbutyl, 1,2,2-trimethylpropyl, 1-ethyl-2,2-dimethylpropyl, 2,2-dimethylpentyl, and 2,3-dimethyl-2-isopropylbutyl.

In formulas (I) to (IV), when $R_1$ represents a linear alkyl group having 1–21 carbon atoms or a branched alkyl group having 3–21 carbon atoms, $R_2$ represents a linear alkyl group having 1–21 carton atoms or a branched alkyl group having 3–21 carbon atoms. Preferably, $R_1$ and $R_2$ independently represent a linear alkyl group having 1–12 carbon atoms or a branched alkyl group having 3–12 carbon atoms. Examples of the linear alkyl groups having 1–21 carbon atoms represented by $R_2$ are the same as those exemplified above for $R_1$.

Alternatively, $R_1$ and $R_2$ may together join to form a ring with an alkylene group having 2–13 carbon atoms. Examples of alkylene groups include ethylene, trimethylene, tetramethylene, pentamethylene, hexamethylene, 1-methyltetramethylene, 2-methyltetramethylene, 1-methylpentamethylene, 2-methylpentamethylene, 3-methylpentamethylene, 1,3-dimethylpentamethylene, 1,5-dimethylpentamethylene, 2,2,4-trimethylpentamethylene, 1-tert-butylpentamethylene, 3-tert-butylpentamethylene, 1-isopropyl-3-methylpentamethylene, and nonamethylene groups. Examples of linear alkyl group having 1–8 carbon atoms or a branched alkyls having 3–8 carbon atoms represented by $R_3$ include methyl, ethyl, propyl, butyl, isobutyl, hexyl, and 2-ethylhexyl, with a preference given to methyl or ethyl.

Of the polyol ether derivatives represented by formulas (I) to (IV), those of which alcohol residue is derived from sorbitol are preferable.

The following are examples (compound names and structures) of polyol ether derivatives represented by formulas (I) to (IV), but the present invention are not limited to the examples:

1, 6-di-O-(1-methylethyl)sorbitol

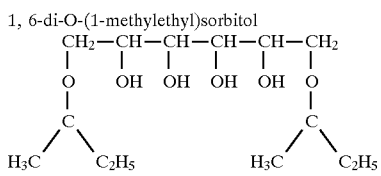

2, 4, 5-tri-O-methyl-1, 3, 6-tri-O-(3, 5, 5-trimethylhexyl)-sorbitol

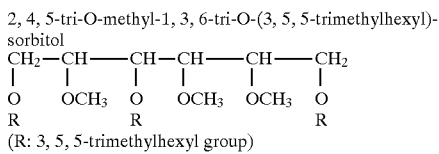

(R: 3, 5, 5-trimethylhexyl group)

1, 6-di-O-(1-methylbutyl)-3, 4-O-(1-methylbutylidene)-sorbitol

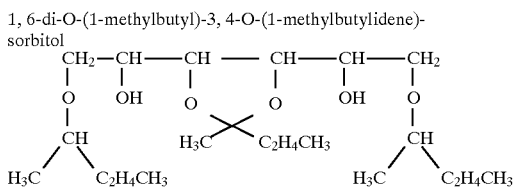

(2) Novel method for producing polyol ether derivatives

A method of the present invention comprises the steps of reacting a hexahydric alcohol represented by formula (V) with a carbonyl compound (ketone or aldehyde) or with a reactive derivative thereof (ketal or acetal) in the presence of acid catalyst to form a cyclic acetal or ketal; and hydrogenating, or hydrogenating and further alkylating the cyclic acetal or ketal to give polyol ether derivatives represented by formulas (VII) to (X). Here, "alkylating" means a reaction that may also be referred to as "alkyl-capping." The reactions proceed as shown in the following steps:

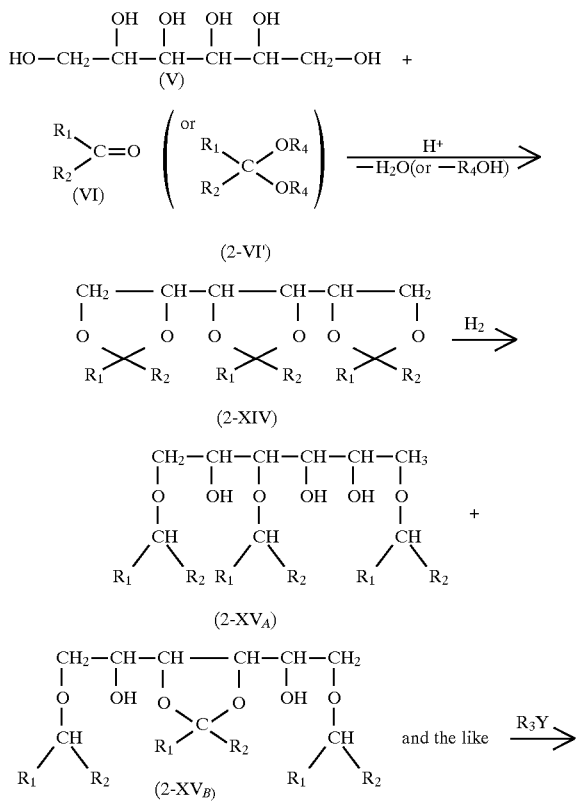

-continued

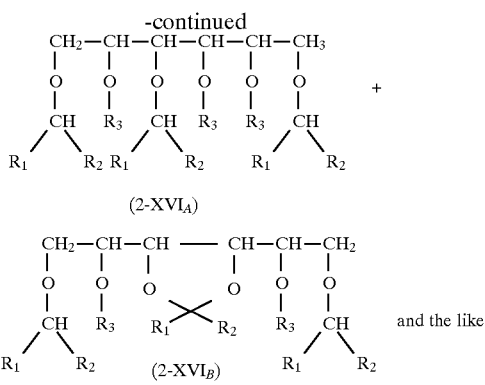

In the above formulas, $R_1$ represents a hydrogen atom, a linear alkyl group having 1–21 carbon atoms or a branched alkyl group having 3–21 carbon atoms. When $R_1$ is a hydrogen atom, $R_2$ is a linear alkyl group having 1–21 carbon atoms or a branched alkyl group having 3–21 carbon atoms, preferably a linear alkyl group having 1–17 carbon atoms or a branched alkyl group having 3–17 carbon atoms, more preferably a linear alkyl group having 1–18 carbon atoms or a branched alkyl group having 3–18 carbon atoms. When $R_1$ is a linear alkyl group having 1–21 carbon atoms or a branched alkyl group having 3–21 carbon atoms, $R_2$ is a linear alkyl group having 1–21 carbon atoms or a branched alkyl group having 3–21 carbon atoms. It is preferable that both $R_1$ and $R_2$ independently are a linear alkyl group having 1–13 carbon atoms or a branched alkyl group having 3–13 carbon atoms.

Examples of linear alkyl groups having 1–8 carbon atoms or a branched alkyl groups having 3–8 carbon atoms represented by $R_3$ include methyl, ethyl, propyl, butyl, isobutyl, hexyl, and 2-ethylhexyl, with a preference given to methyl or ethyl.

$R_4$ represents a linear alkyl group having 1–6 carbon atoms or a branched alkyl group having 3–6 carbon atoms. Y represents a residue of an alkylating agent.

In brief, the polyol ether derivatives of the present invention are produced by the following steps:

reacting a hexahydric alcohol such as sorbitol and mannitol represented by formula (V) with a carbonyl compound such as a ketone and an aldehyde represented by formula (VI) for dehydration, or with a reactive derivative thereof represented by formula (2-VI') for dealcoholization, both in the presence of acid catalyst to give a cyclic acetal or ketal represented by formula (2-XIV); and hydrogenating the cyclic acetal or ketal to give a polyol ether or a polyol ether acetal or ketal (here, "polyol ether acetal or ketal" means partially etherified and partially acetalized or ketalized polyol); or further alkylating the polyol ether or the polyol ether acetal or ketal to give an alkylated (alkyl-capped) ether represented by formulas (2-XVI$_A$) and (2-XVI$_B$) after hydrogenation as mentioned above.

The starting materials used in the above-mentioned reactions will be described in detail.

Hexahydric alcohol

Examples of hexahydric alcohols usable in the present invention are those represented by formula (V), which include hexytols obtained by reducing hexoses, such as sorbitol, mannitol, galactitol, iditol, talitol, and allitol. From the view point of availability and cost, sorbitol is the most preferable.

Carbonyl compound

The carbonyl compounds usable in the present invention and represented by formula (VI) are ketones and aldehydes. Ketones are readily obtained by high temperature decarboxylating dimerization of fatty acids, catalytic oxidation of olefins (Wacker process), oxidation-dehydrogenation of secondary alcohols, and oxidation of cycloalkanes. Ketones obtained by Wacker process show a molecular weight distribution, but they can be separated and purified by rectification. The ketones usable in the present invention are exemplified below, but not limited to these examples.

Examples of methyl alkyl ketones include acetone, methyl ethyl ketone, methyl propyl ketone, methyl butyl ketone, methyl amyl ketone, methyl hexyl ketone, methyl heptyl ketone, methyl octyl ketone, methyl nonyl ketone, methyl undecyl ketone, and methyl heptadecyl ketone.

Examples of dialkyl ketones include diethyl ketone, ethyl propyl ketone, ethyl butyl ketone, dipropyl ketone, ethyl pentyl ketone, ethyl hexyl ketone, dibutyl ketone, depentyl ketone, dihexyl ketone, diundecyl ketone, and diheptadecyl ketone.

Examples of polybranched ketones include methyl isopropyl ketone, methyl sec-butyl ketone, methyl isobutyl ketone, ethyl isopropyl ketone, methyl tert-butyl ketone, diisopropyl ketone, methyl isoamyl ketone, isopropyl propyl ketone, methyl neopentyl ketone, ethyl tert-butyl ketone, 6-methyl-2-heptanone, 4-methyl-3-heptanone, 2-methyl-3-heptanone, 5-methyl-3-heptanone, diisobutyl ketone, and 6,10-dimethyl-2-undecanone.

Examples of cyclic ketones include cyclopropanone, cyclobutanone, cyclopentanone, cyclohexanone, 2-methyl cyclopentanone, 3-methylcyclopentanone, 2-methylcyclohexanone, 3-methylcyclohexanone, 4-methylcyclohexanone, cycloheptanone, 2,4-dimethylcyclohexanone, 2,6-dimethylcyclohexanone, 3,3,5-trimethylcyclohexanone, 2-tert-butylcyclohexanone, 4-tert-butylcyclohexanone, 2-isopropyl-4-methylcyclohexanone, and cyclodecanone.

Examples of cyclic alkyl ketones include methyl cyclohexyl ketone, and 5-(2',2',5'-trimethylcyclohexyl)-2-pentanone.

Aldehydes used in the present invention are those readily prepared by the following methods: dehydrogenation of fatty alcohols, hydroformylation of olefins (oxo method), Rosenmund reduction of fatty acid chlorides, and direct hydrogenation of fatty acids. In the case of the oxo method, both linear and branched aldehydes are produced, but they can be separated and purified by rectification.

The aldehydes mentioned below are just examples usable in the present invention and are not limitative.

Examples of linear alkyl aldehydes include acetaldehyde, propionaldehyde, butyraldehyde, valeraldehyde, caproaldehyde, heptanal, octanal, decanal, dodecanal, tetradecanal, octadecanal, and behenaldehyde.

Examples of α-branched alkyl aldehydes include isobutyraldehyde, 2-methylbutyraldehyde, 2-methylpentanal, 2-ethylbutanal, 2-methylhexanal, 2-ethylpentanal, 2-methylheptanal, 2-ethylhexanal, and 2-propylpentanal.

Examples of α- and other polybranched alkyl aldehydes having one or more branches at positions other than α-position include 2,3-dimethylbutanal, 2,4,4-trimethylpentanal, and 2-isopropyl-5-methylhexanal.

Other examples of other branched alkyl aldehydes having one or more branches at positions other than α-position include isovaleraldehyde, 3-methylpentanal, 4-methylpentanal, 3,3-dimethylbutanal, 3-methylhexanal, 4-methylhexanal, 5-methylhexanal, 3,5,5-trimethylhexanal, isodecylaldehyde, 3,7-dimethyloctanal, and isooctadecanal.

Examples of cyclic alkyl aldehydes include cyclopentylacetaldehyde, and cyclohexylacetaldehyde.

Reactive derivatives of carbonyl compounds

Reactive derivatives of carbonyl compounds used in the present invention are ketals and acetals represented by formula (2-VI') which can readily be obtained by the reaction of a ketone or aldehyde as mentioned above with a lower alcohol having 1–6 carbon atoms in the presence of an acid catalyst. Examples of lower alcohols having 1–6 carbon atoms which give $R_4$ residue include methanol, ethanol, propanol, isopropanol, butanol, isobutanol, sec-butanol, tert-butanol, amyl alcohol, isoamyl alcohol, neopentyl alcohol, 1-methylbutanol, 1,1-dimethylpropanol, 1-ethylpropanol, hexanol, isohexanol, 2-ethylbutanol, 1-methylamyl alcohol, 1,3-dimethylbutanol, and 1-ethylbutanol.

Ketalization

In the present invention, the reaction between a hexahydric alcohol represented by formula (V) and a ketone is ketalization. The molar ratio of the ketone to the hexahydric alcohol is in the range of from 1 to 15, preferably from 1.5 to 7.5. This reaction requires an acidic catalyst, such as p-toluenesulfonic acid, methanesulfonic acid, and sulfuric acid in an amount of 0.05 to 10 mole %, preferably 0.1 to 7 mole %, and more preferably 0.5 to 5 mole % to the amount of the hexahydric alcohol represented by formula (V).

The above reaction may be carried out with or without solvents. Solvents usable in the present invention include inert solvents, such as xylene, toluene, benzene, octane, isooctane, heptane, hexane, cyclohexane, pentane, ligroin, and petroleum ether. These solvents are used singly or in combination. The reaction temperature depends upon the boiling point of the ketone used, and the reaction is normally carried out at a temperature of from 40° to 160° C., preferably from 60° to 100° C., while removing the water formed in the process of the reaction. There are also some cases where the reaction can effectively be carried out under a reduced pressure. In the above temperature range, the reaction can favorably proceed and coloration due to side reactions is less likely to occur. Also, the reaction may be carried out in a nitrogen stream, nitrogen atmosphere, or dry air. The reaction time varies with reaction conditions employed, but it is generally preferred to continue the reaction for 5 to 200 hours. The cyclic ketals obtained (2-XIV) are neutralized and subjected to pretreatments, such as filtration and washing. Then, the ketals can be purified by such means as adsorption, crystallization, and distillation.

Acetalization

In the present invention, the reaction between a hexahydric alcohol represented by formula (V) and an aldehyde is acetalization. The molar ratio of the aldehyde to the hexahydric alcohol is in the range of from 1 to 6, preferably from 1.5 to 3.8. This reaction requires an acidic catalyst, such as p-toluenesulfonic acid, methanesulfonic acid, and sulfuric acid, in an amount of 0.01 to 5 mole %, preferably 0.05 to 3 mole %, and more preferably 0.1 to 2 mole % to the amount of the hexahydric alcohol represented by formula (V).

The above reaction may be carried out with or without solvents. Solvents usable in the present invention include inert solvents, such as xylene, toluene, benzene, octane, isooctane, heptane, hexane, cyclohexane, pentane, ligroin, and petroleum ether. These solvents are used singly or in combination. The reaction temperature depends upon the boiling point of the aldehyde used, and the reaction is normally carried out at a temperature of from 20° to 130° C., preferably from 40° to 100° C., while removing the water in the process of the reaction. There are also some cases where the reaction can effectively proceed under a reduced pressure. In the above temperature range, the reaction can favorably proceed and coloration due to side reactions is less likely to occur. Also, the reaction may be carried out in a nitrogen stream, nitrogen atmosphere, or dry air. The reaction time varies with reaction conditions employed, but it is generally preferred to continue the reaction for 1 to 30 hours. The cyclic acetals obtained (2-XIV) are neutralized and subjected to pretreatments, such as filtration and washing. Then, the acetals can be purified by conventional means, such as adsorption, crystallization, and distillation.

Transketalization

In the present invention, the reaction between a hexahydric alcohol represented by formula (V) and a ketal (2-VI'), a reactive derivative of ketone, is transketalization. The molar ratio of the ketal to the hexahydric alcohol is in the range of from 1 to 15, preferably from 1.5 to 7.5. This reaction requires an acidic catalyst, such as p-toluenesulfonic acid, methanesulfonic acid, and sulfuric acid, in an amount of 0.05 to 10 mole %, preferably 0.1 to 7 mole %, and more preferably 0.5 to 5 mole % to the amount of the hexahydric alcohol represented by formula (V).

The above reaction may be carried out with or without solvents. Solvents usable in the present invention include inert solvents, such as xylene, toluene, benzene, octane, isooctane, heptane, hexane, cyclohexane, pentane, ligroin, and petroleum ether. These solvents are used singly or in combination. Though the reaction temperature depends upon the boiling points of the ketal (2-VI') used and the lower alcohol formed, the reaction is carried out at a temperature of from 40° to 160° C., preferably from 60° to 130° C., while removing the lower alcohol formed in the process of the reaction. There are also some cases where the reaction can effectively be carried out under a reduced pressure. In the above temperature range, the reaction can favorably proceed and coloration due to side reactions is less likely to occur. Also, the reaction may be carried out in a nitrogen stream, nitrogen atmosphere, or dry air. The reaction time varies with reaction conditions employed, but it is generally preferred to continue the reaction for 5 to 200 hours. The cyclic ketals obtained (2-XIV) are neutralized and subjected to pretreatments, such as filtration and washing. Then, the cyclic ketals can be purified by conventional means, such as adsorption, crystallization, and distillation.

Transacetalization

In the present invention, the reaction between a hexahydric alcohol represented by formula (V) and an acetal (2-VI'), a reactive derivative of aldehyde, is transacetalization. The molar ratio of the acetal (2-VI') to the hexahydric alcohol is in the range of from 1.5 to 6, preferably from 2.7 to 3.8. This reaction requires an acidic catalyst, such as p-toluenesulfonic acid, methanesulfonic acid, and sulfuric acid, in an amount of 0.01 to 5 mole %, preferably 0.05 to 3 mole %, and more preferably 0.1 to 2 mole % to the amount of the hexahydric alcohol represented by formula (V).

The above reaction may be carried out with or without solvents. Solvents usable in the present invention include inert solvents, such as xylene, toluene, benzene, octane, isooctane, heptane, hexane, cyclohexane, pentane, ligroin, and petroleum ether. These solvents are used singly or in combination. The reaction temperature depends upon the boiling points of the acetal used and the lower alcohol formed, and the reaction is normally carried out at a temperature of from 20° to 150° C., preferably from 40° to 130° C., while removing the lower alcohol formed in the process of the reaction. There are also some cases where the reaction can effectively proceed under a reduced pressure. In the above temperature range, the reaction can favorably proceed and coloration due to side reactions is less likely to occur. Also, the reaction may be carried out in a nitrogen stream, nitrogen atmosphere, or dry air. The reaction time varies with reaction conditions employed, but it is generally preferred to continue the reaction for 1 to 30 hours. The cyclic acetals obtained (2-XIV) are neutralized and subjected to pretreatments, such as filtration and washing. Then, the acetals can be purified by conventional means, such as adsorption, crystallization, and distillation.

Hydrogenation

The hydrogenation of the cyclic ketal or cyclic acetal represented by formula (2-XIV) can be carried out using a conventional hydrogenolysis catalyst, such as palladium, rhodium, ruthenium, and platinum, in an amount of from 5 to 5000 ppm to the amount of cyclic acetal or cyclic ketal, under normal to 250 kg/cm$^2$ of hydrogen pressure, at a temperature of from 50° to 250° C., for 1 to 30 hours. The above hydrogenolysis catalysts may be carried on the surface of carriers, such as carbon, alumina, silica, diatomaceous earth, and titanium oxide, at a ratio of 0.1 to 20%. As for hydrogenolysis catalyst, palladium, especially having a pH of 5 to 8, is particularly preferable. It is also preferred to remove moisture from the catalyst before use. This reaction may be carried out with or without solvents. When a solvent is used, the following inert solvents can be used singly or in combination: decane, octane, isooctane, heptane, hexane, and cyclohexane. The starting materials of cyclic acetals or ketals, such as hexahydric alcohols represented by formula (V), aldehydes, and ketones, may be added to the reaction system. Acidic substances, such as phosphoric acid, may be added in a slight amount. The reaction may be carried out in a closed system or under a hydrogen stream.

In this hydrogenation reaction, the bond between carbon and oxygen atoms in an acetal or ketal is reductively cleaved to give an ether and alcohol, and intermolecular transformation of acetals or ketals occurs at the same time. Accordingly, the starting materials of triacetal or triketal generally can yield a mixture of alkyl ethers with different numbers of substituents ranging from 1 to 5. In the resulting alkyl ethers having the same number of substituents, those etherified at 1 and/or 6 positions are predominant. When the reaction is discontinued on the way, ether alcohols having acetal or ketal rings can be obtained. When alkyl ethers having a smaller number of alkyl or alkylidene substituents are to be obtained, acetals or ketals which are prepared by using an aldehyde or a ketone or a reactive derivative thereof in an amount smaller than the equivalent of a hexahydric alcohol may be subjected to the hydrogenation. Alkyl ethers with a smaller number of substituents can also be obtained by adding a hexahydric alcohol to a triacetal or a triketal, and carrying out the hydrogenation reaction.

When alkyl ethers having a smaller number of alkyl substituents and no acetal or ketal rings are to be obtained, hydrogenation may be discontinued on the way and hydrolysis is carried out in a methanol or ethanol aqueous solution using p-toluensulfonic acid, sulfuric acid, or hydrochloric acid as a catalyst.

When alkyl ethers having a larger number of alkyl substituents are to be obtained in a larger quantity, an acetal or ketal is further added to the hydrogenation reaction system.

The thus-obtained mixture of polyol ethers (2-XV$_A$), the mixture of polyol ether acetals (2-XV$_B$), or the mixture of polyol ether ketals (2-XV$_B$), each mixture containing hydrogenation products with different numbers of alkyl substituents, may be subjected to the subsequent alkylation directly, or, if necessary, after a desired polyol ether or the like is isolated.

The isolation of a desired polyol ether or the like from the reaction mixtures can be carried out by conventional means after removing the catalyst used by filtration. For example, evaporation of solvent, washing, recrystallization, distillation, and chromatography may be employed solely or in combination.

Alkylation (alkyl-capping)

Ether compounds represented by formulas (2-XVI$_A$) and (2-XVI$_B$) are obtained by treating the hydroxyl groups of the polyol ethers (2-XV$_A$) or polyol ether ketals or acetals (2-XV$_B$) obtained by the above-mentioned process with a base, such as Na, NaH, NaOCH$_3$, NaOH, and KOH, to give a corresponding alcoholate, and treating the alcoholate with an alkylating agent, such as an alkyl halide, dialkyl sulfate, and alkyl tosylate, to alkylate the hydroxyls of the polyol ethers or polyol ether ketals or acetals.

The alkyl halides used in the above reaction include the following halogenated lower alkyls: chlorides of linear alkyls, such as methyl chloride, ethyl chloride, propyl chloride, butyl chloride, amyl chloride, hexyl chloride, and octyl chloride; chlorides of branched alkyls such as isopropyl chloride, isobutyl chloride, sec-butyl chloride, isoamyl chloride, neopentyl chloride, 1-methylbutyl chloride, 1-ethylpropyl chloride, isohexyl chloride, 2-ethylbutyl chloride, 1-methylamyl chloride, 1-ethylbutyl chloride, and 2-ethylhexyl chloride; bromides of linear alkyls, such as methyl bromide, ethyl bromide, propyl bromide, butyl bromide, amyl bromide, and hexyl bromide; bromides of branched alkyls, such as isopropyl bromide, isobutyl bromide, sec-butyl bromide, isoamyl bromide, neopentyl bromide, 1-methylbutyl bromide, 1-ethylpropyl bromide, isohexyl bromide, 2-ethylbutyl bromide, 1-methylamyl bromide, 1-ethylbutyl bromide, and 2-ethylhexyl bromide; iodides of linear alkyls, such as methyl iodide, ethyl iodide, propyl iodide, butyl iodide, amyl iodide, and hexyl iodide; iodides of branched alkyls, such as isopropyl iodide, isobutyl iodide, sec-butyl iodide, isoamyl iodide, neopentyl iodide, 1-methylbutyl iodide, 1-ethylpropyl iodide, isohexyl iodide, 2-ethylbutyl iodide, 1-methylamyl iodide, 1,3-dimethylbutyl iodide, and 1-ethylbutyl iodide. In view of reactivity, a preference is given to primary alkyl halides. It is also preferred that these alkyl halides have a boiling point of not higher than 50° C. so that chlorine, bromine or iodine will not remain after the reaction.

Examples of dialkyl sulfates are the following lower dialkyl sulfates: linear dialkyl sulfates, such as dimethyl sulfate, diethyl sulfate, dipropyl sulfate, dibutyl sulfate, diamyl sulfate, and dihexyl sulfate; and branched dialkyl sulfates, such as diisopropyl sulfate, diisobutyl sulfate, di-sec-butyl sulfate, diisoamyl sulfate; dineopentyl sulfate, di(1-methylbutyl) sulfate, di(1-ethylpropyl) sulfate, diisohexyl sulfate, di(2-ethylbutyl) sulfate, di(1-methylamyl) sulfate, and di(1-ethylbutyl) sulfate. In view of reactivity, a preference is given to primary alkyl sulfates.

Examples of alkyl tosylates are the following lower alkyl tosylates: linear alkyl tosylates, such as methyl tosylate, ethyl tosylate, propyl tosylate, butyl tosylate, amyl tosylate, and hexyl tosylate; and branched alkyl tosylates, such as isopropyl tosylate, isobutyl tosylate, sec-butyl tosylate, isoamyl tosylate, neopentyl tosylate, 1-methylbutyl tosylate, 1-ethylpropyl tosylate, isohexyl tosylate, 2-ethylbutyl tosylate, 1-methylamyl tosylate, 1,3-dimethyl tosylate, and 1-ethylbutyl tosylate. In view of reactivity, a preference is given to primary alkyl tosylates.

In the alkylation process, the molar ratio of a base to a hydroxyl group of polyol ethers (2-XV$_A$) or polyol ether ketals or acetals (2-XV$_B$) is 1.0 to 3.0, preferably 1.0 to 1.5; and the molar ratio of an alkylating agent to the hydroxyl group is 1.0 to 3.0, preferably 1.0 to 1.5. The alcoholate forming reaction is carried out in an inert solvent or in a mixture of solvents, the solvents including xylene, toluene, benzene, octane, isooctane, heptane, hexane, cyclohexane, pentane, ligroin, petroleum ether, dimethyl sulfoxide, and 1,2-dimethoxydiethane, at a temperature in the range of from room temperature to 110° C., the temperature depending on the boiling point and stability of the solvents used. Then, O-alkylation is carried out by adding an alkylating agent dropwise at a temperature of from room temperature to 130° C., the temperature depending on the reactivity of the alkylating agent. The alcoholate forming reaction is continued for 0.5 to 2 hours. The reaction time for O-alkylation depends on the degree of exotherm, and it is continued preferably for 0.5 to 6 hours as long as the exothermic reaction can be kept under control. After the completion of the reaction, alcoholates and the alkylating agents which remain unchanged are decomposed by adding an aqueous solution of an alkali, such as sodium hydroxide. After the resulting ether compounds represented by formulas (2-XVI$_A$) and (2-XVI$_B$) are subjected to pretreatments, such as extraction, filtration, and washing, and they are purified by such a means as adsorption, steaming, dehydration, and distillation.

(3) A working fluid composition for a refrigerating machine comprising a refrigeration oil containing polyol ether derivatives as a base oil and a hydrofluorocarbon The working fluid composition for a refrigerating machine of the present invention is characterized by comprising polyol ether derivatives represented by formula (XI) as a base oil of a refrigeration oil.

In formula (XI), $R^1$ to $R^6$ may be identical or different, each representing a linear alkyl group having 1–14 carbon atoms, a branched alkyl group having 3–14 carbon atoms or a cyclic alkyl group having 3–14 carbon atoms. The total number of carbon atoms of $R^1$ to $R^6$ is in the range of from 8 to 40.

Generally, the compatibility of a compound used as a base oil with a hydrofluorocarbon becomes better as the polarity increases, whereas the insulating property becomes better as the polarity decreases. Therefore, it is important to appropriately balance the polarity of a compound used as a base oil of a refrigeration oil.

In the case of an alkyl ether having an alcohol residue with a small number of hydroxyls, e.g., 3 to 4 hydroxyls, it is required for the alkyl group of the ether to have a larger number of carbon atoms to get an appropriate viscosity. This makes the polarity of the alkyl ether lower, and thereby makes the compatibility with a hydrofluorocarbon poor. On the other hand, in the case of an alkyl ether having an alcohol residue with a large number of hydroxyls, e.g., 12 to 13 hydroxyls, it is required for the alkyl group of the ether to have a smaller number of carbon atoms to get an appropriate viscosity. This makes the polarity of the alkyl ether higher and thereby makes the insulating property poor. Therefore, an alcohol residue having 6 hydroxyls is particularly preferable for appropriately balancing the above factors.

The hexahydric alcohols, which give the hexahydric alcohol residue (the structure which remains after deleting $R^1O$— to $R^6O$— from formula (XI)), include the hexahydric alcohols exemplified as the starting materials set forth in "(2) A novel method for producing polyol ether derivatives." Among the examples, sorbitol is the most preferable in terms of availability and cost.

The linear alkyl group having 1–14 carbon atoms, the branched alkyl group having 3–14 carbon atoms or the cyclic alkyl group having 3–14 carbon atoms represented by $R^1$ to $R^6$ in formula (XI) are those as exemplified below.

Among the examples of linear alkyl groups having 1–21 carbon atoms or branched alkyl groups having 3–21 carbon atoms represented by $R_1$ set forth in "(1) Novel polyol ether derivatives," those having 1–14 carbon atoms can be examples of the alkyls represented by $R^1$ to $R^6$ in formula (XI). Also, alkyls having a tertiary and no hydrogen atom at α-position can be exemplified by 1,1-dimethylethyl, 1-methylcyclopropyl, 1,1-dimethylpropyl, 1-methylcyclobutyl, 1,1-dimethylbutyl, 1,1,2-trimethylpropyl, 1-methylcyclopentyl, 1,1-dimethylpentyl, 1-methyl-1-ethylbutyl, 1,1-diethylpropyl, and 1,1-diethylbutyl.

Examples of α-cyclic alkyl groups include cyclopropyl, cyclobutyl, cyclopentyl, cyclohexyl, cycloheptyl, 2-methylcyclopentyl, 3-methylcyclopentyl, 2-methylcyclohexyl, 3-methylcyclohexyl, 4-methylcyclohexyl, 2,4-dimethylcyclohexyl, 2,6-dimethylcyclohexyl, 3,3,5-trimethylcyclohexyl, 2-tert-butylcyclohexyl, 4-tert-butylcyclohexyl, 2-isopropyl-4-methylcyclohexyl, and cyclodecyl.

Examples of cycloalkyl groups include cyclopentylmethyl, cyclohexylmethyl, 1-methyl-4-(2'2'5'-trimethylcyclohexyl)butyl, and 1-cyclohexylethyl.

Examples of alkyl groups having tert-carbons and no hydrogen atoms at both α- and β-positions include 1,1,2,2-tetramethylpropyl, 1,1,2,2-tetramethylbutyl, and 1,1,2,2-tetramethylhexyl.

For satisfactory compatibility with hydrofluorocarbons and insulating property, the ratio of the total number of carbon atoms to the total number of oxygen atoms in a molecule (C/O) is preferably in the range of from 2.5 to 7.5, more preferably 3.0 to 7.0, even more preferably 3.0 to 7.0, and particularly preferably 4.0 to 6.0.

Accordingly, the total number of carbon atoms is normally in the range of 8 to 40, preferably 9 to 39, more preferably 12 to 36, and still more preferably 18 to 30. When the total number of carbon atoms is less than 8, it results in poor insulating property; when it is higher than 40, compatibility with hydrofluorocarbons becomes poor.

In order to get better compatibility with hydrofluorocarbons, branched and cyclic alkyls are preferred to linear alkyls. Between branched and cyclic alkyls, a preference is given to branched alkyls. Alkenyls and alkinyls having unsaturated bonds are not preferable because of poor thermal stability.

The names and structures of the polyol ether derivatives represented by formula (XI) are listed below. However, they are not limitative, and compounds represented by formulas (XIII$_{AA}$) and (XIII$_{BB}$) are also included in the polyol ether derivatives of the present invention.

1) 2,3,4,5-tetra-O-methyl-1,6-di-O-(3,5,5-trimethylhexyl) sorbitol

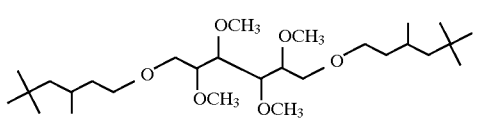

2) 2,4,5-tri-O-methyl-1,3,6-tri-O-(3,5,5-trimethylhexyl) sorbitol

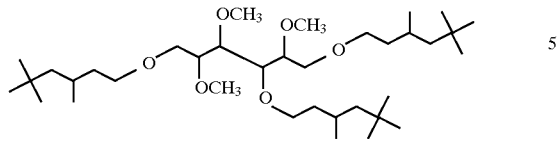

3) 1,6-di-O-(3,5,5-trimethylhexyl)-di-O-methyl-di-O-(3,5,5-trimethylhexyl)sorbitol

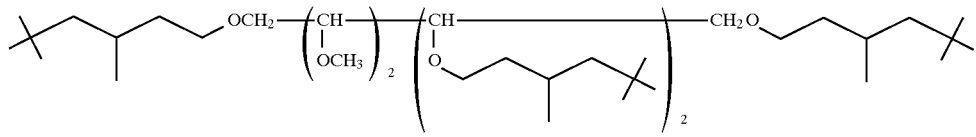

(Except for both ends, the repeating units may be arranged at random or in block form.)

4) 2,3,4,5,6-penta-O-methyl-1-O-(3,5,5-trimethylhexyl)-sorbitol

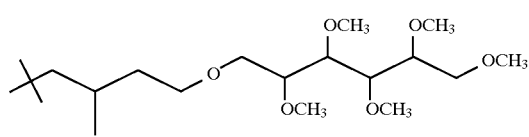

5) 2,3,4,5-tetra-O-methyl-1,6-di-O-(1,3-dimethylbutyl) sorbitol

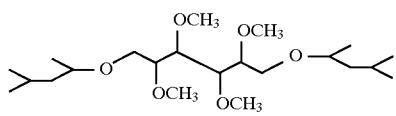

6) 2,4,5-tri-O-methyl-1,3,6-tri-O-(1,3-dimethylbutyl) sorbitol

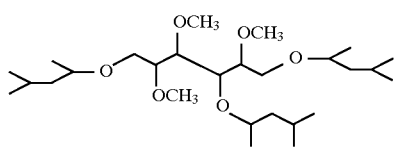

7) 1,6-di-O-(1,3-dimethylbutyl)-di-O-methyl-O-(1,3-dimethylbutylidene)sorbitol

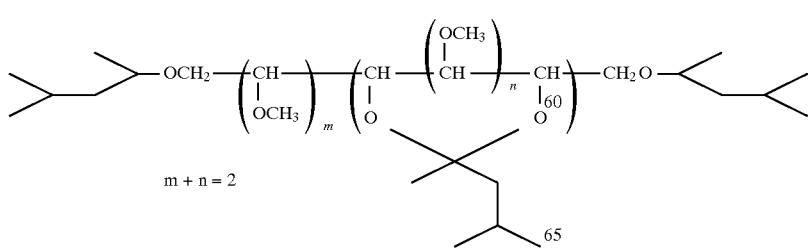

(Except for both ends, the repeating units may be arranged at random or in block form.)

8) 1,6-di-O-(1,3-dimethylbutyl)-O-methyl-O-(1,3-dimethylbutyl)-O-(1,3-dimethylbutylidene)sorbitol 13) 1,6-di-O-(1-methylpropyl)-di-O-ethyl-di-O-(1-methylpropyl)sorbitol

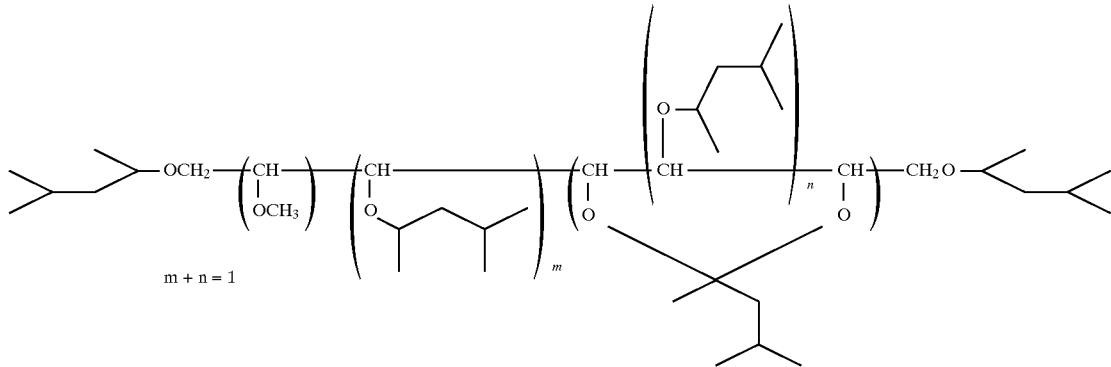

(Except for both ends, the repeating units may be arranged at random or in block form.)

9) 2,3,4,5-tetra-O-methyl-1,6-di-O-(1-methylpropyl)sorbitol

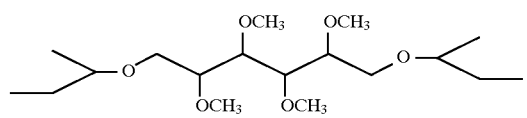

10) 2,4,5-tri-O-methyl-1,3,6-tri-O-(1-methylpropyl)sorbitol

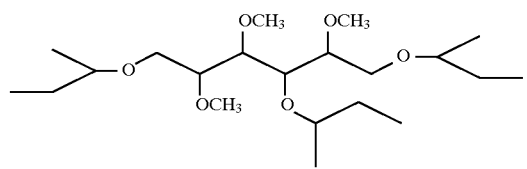

11) 1,6-di-O-(1-methylpropyl)-di-O-methyl-O-(1-methylpropylidene)sorbitol

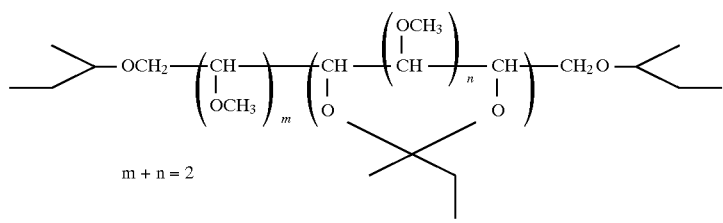

(Except for both ends, the repeating units may be arranged at random or in block form.)

12) 1,6-di-O-(1-methylpropyl)-di-O-methyl-di-O-(1-methylpropyl)sorbitol

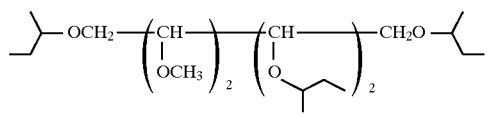

(Except for both ends, the repeating units may be arranged at random or in block form.)

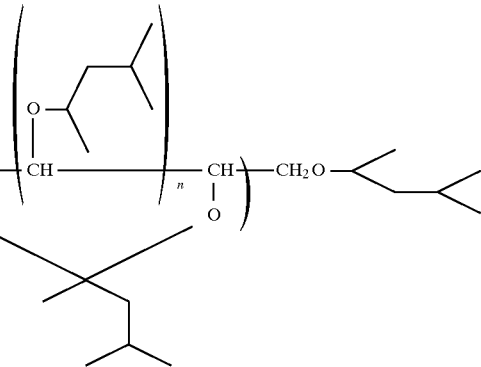

(Except for both ends, the repeating units may be arranged at random or in block form.)

14) 2,4,5-tri-O-ethyl-1,3,6-tri-O-(1,3-dimethylbutyl)sorbitol

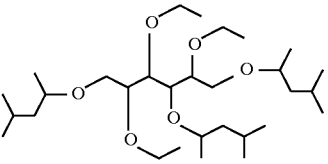

15) 2,3,4,5-tetra-O-methyl-1,6-di-O-(cyclohexyl)sorbitol

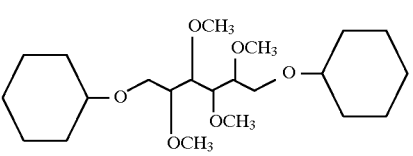

16) 2,4,5-tri-O-methyl-1,3,6-tri-O-(cyclohexyl)sorbitol

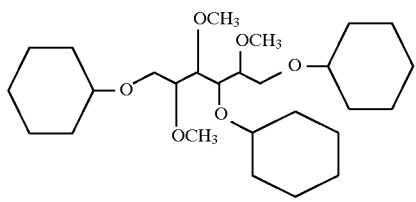

17) 1,6-di-O-(cyclohexyl)-di-O-methyl-di-O-(cyclohexyl)sorbitol

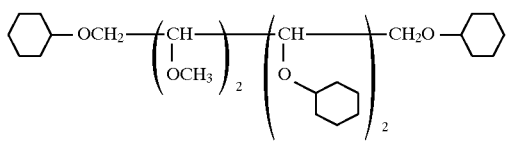

(Except for both ends, the repeating units may be arranged at random or in block form.)

18) 2,3,4,5-tetra-O-isopropyl-1,6-di-O-(cyclohexyl)sorbitol

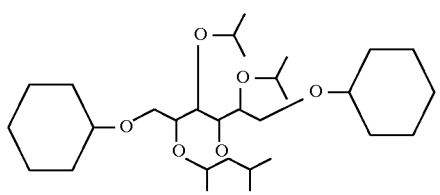

19) O-(3,5,5-trimethylhexyl)-di-O-(1,3-dimethylbutyl)-tri-O-(ethyl)sorbitol

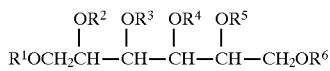

$R^1$–$R^6$: 3,5,5-trimethylhexyl (1 mole), 1,3-dimethylbutyl (2 moles), ethyl (3 moles)

20) O-(3,5,5-trimethylhexyl)-di-O-(2-methylpropyl)-tri-O-(butyl)sorbitol

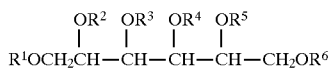

$R^1$–$R^6$: 3,5,5-trimethylhexyl (1 mole), 2-methylpropyl (2 moles), butyl (3 moles)

21) di-O-(2-ethylhexyl)-O-(1-methylpropyl)-tri-O-(methyl)sorbitol

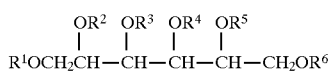

$R^1$–$R^6$: 2-ethylhexyl (2 moles), 1-methylpropyl (1 mole), methyl (3 moles)

22) di-O-(1-isopropyl-2-methylpropyl)-O-(1-methylpropyl)-tri-O-(ethyl)sorbitol

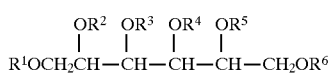

$R^1$–$R^6$: 1-isopropyl-2-methylpropyl (2 moles), 1-methylpropyl (1 mole), ethyl (3 moles)

23) tri-O-(1,3-dimethylbutyl)-O-(cyclohexyl)-di-O-(methyl)sorbitol

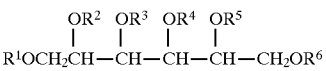

$R^1$–$R^6$: 1,3-dimethylbutyl (3 moles), cyclohexyl (1 mole), methyl (2 moles)

24) di-O-(1,3-dimethylbutyl)-di-O-(1-methylpropyl)di-O-(2-methylpropyl)

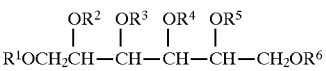

$R^1$–$R^6$: 1,3-dimethylbutyl (2 moles), 1-methylpropyl (2 moles), 2-methylpropyl (2 moles)

25) 2,4,5-tri-O-ethyl-1,3,6-tri-O-(1-methylpropyl)sorbitol

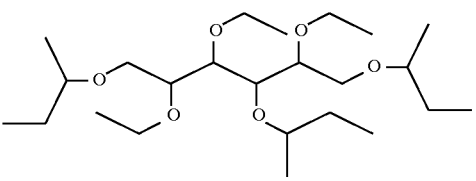

26) 2,3,4,5,6-penta-O-methyl-1-O-(1,3-dimethylbutyl)sorbitol

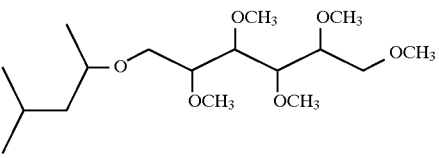

27) 1,6-di-O-(1,3-dimethylbutyl)-di-O-methyl-di-O-(1,3-dimethylbutyl)sorbitol

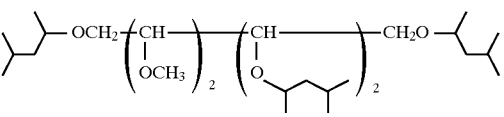

(Except for both ends, the repeating units may be arranged at random or in block form.)

The above polyol ether derivatives represented by formula (XI) can be produced by various methods, For example, it can be produced by the reaction of a hexitol alcoholate, a reactive derivative of hexitol, with an alkyl halide. However, halogen, such as chlorine, bromine or iodine, undesirably remains in the product obtained by this method, which impairs thermal stability of the product.

Therefore, the method described above in "(2) Novel method for producing polyol ether derivatives" is recommended as an economical and simple method because it does not use compounds having halogen, such as chlorine, bromine, or iodine.

Specifically, the polyol ether derivatives represented by formula (XI) is synthesized by the steps of reacting a hexahydric alcohol represented by formula (V) with one or more carbonyl compounds (ketone or aldehyde) represented by formula (XII) for ketalization or acetalization, or with reactive derivatives of the carbonyl compounds (ketal or acetal) for transketalization or transacetalization to obtain cyclic ketals or cyclic acetals; hydrogenating the cyclic ketals or the cyclic acetals to obtain polyol ethers; and alkylating the polyol ethers to give polyol ether derivatives.

In formula (XII), $R^7$ represents a hydrogen atom, a linear alkyl group having 1–13 carbon atoms, a branched alkyl group having 3–13 carbon atoms or a cyclic alkyl group having 3–13 carbon atoms, and $R^8$ represents a linear alkyl group having 1–13 carbon atoms, a branched alkyl group having 3–13 carbon atoms or a cyclic alkyl group having 3–13 carbon atoms with the proviso that $R^7$ and/or $R^8$ have at least one hydrogen atom at α-position to the carbonyl group and the total number of carbon atoms of $R^7$ and $R^8$ is 1–13; and $R^7$ and $R^8$ may together join to form a ring with an alkylene group having 2–13 carbon atoms.

The following is an example scheme of the above reaction.

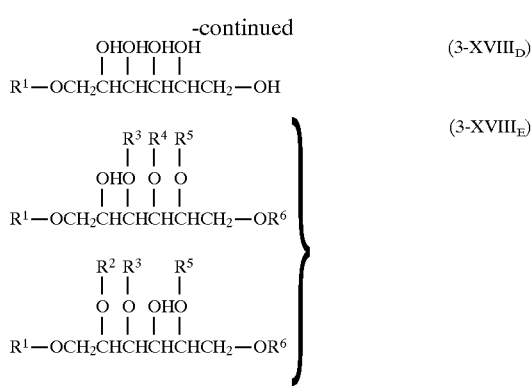

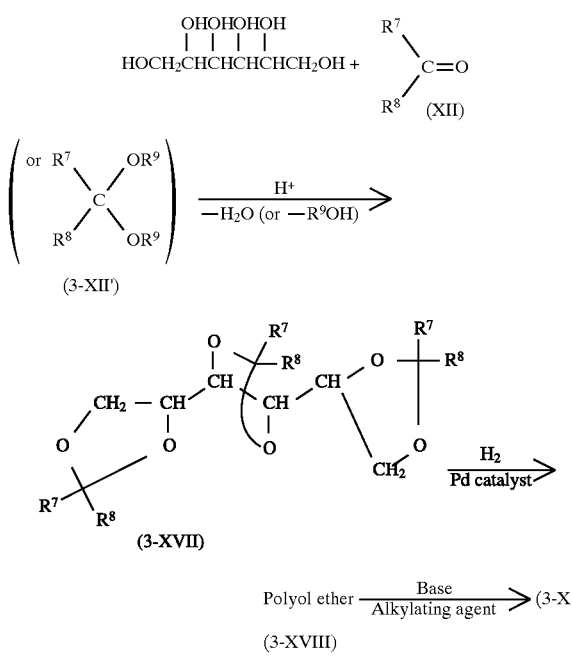

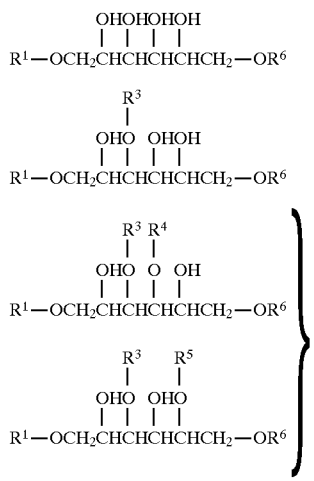

This reaction mainly produces, as a polyol ether (3-XVIII), two-molar adducts (3-XVIII$_A$), three-molar adducts (3-XVIII$_B$), and four-molar adducts (3-XVIII$_C$), with small quantities of one-molar adducts (3-XVIII$_D$) and five-molar adducts (3-XVIII$_E$).

$$R^1{-}OCH_2CHCHCHCH_2{-}OR^6 \quad \text{(3-XVIII}_A\text{)}$$
with OHOHOHOH above $$R^1{-}OCH_2CHCHCHCHCH_2{-}OR^6 \quad \text{(3-XVIII}_B\text{)}$$
with $R^3$, OHO OHOH above $$R^1{-}OCH_2CHCHCHCHCH_2{-}OR^6 \quad \text{(3-XVIII}_C\text{)}$$
with $R^3 R^4$, OHO O OH above $$R^1{-}OCH_2CHCHCHCHCH_2{-}OR^6$$
with $R^3 \ R^5$, OHO OHO above $$R^1{-}OCH_2CHCHCHCHCH_2{-}OH \quad \text{(3-XVIII}_D\text{)}$$
with OHOHOHOH above $$R^1{-}OCH_2CHCHCHCHCH_2{-}OR^6 \quad \text{(3-XVIII}_E\text{)}$$
with $R^3 R^4 R^5$, OHO O O above $$R^1{-}OCH_2CHCHCHCHCH_2{-}OR^6$$
with $R^2 R^3 \ \ R^5$, O O OHO above In the above formulas, $R^1$ to $R^6$ have the same meanings as those in formula (XI). However, in the above-mentioned reaction scheme, $R^1$ to $R^6$ correspond to the residues of the carbonyl compound represented by formula (XII) or the residues of the reactive derivative thereof, and, therefore, can be represented by the following formula:

alkyl group: $-CHR^7R^8$.

The polyol ethers (3-XVIII) can be separated to the compounds (3-XVIII$_A$) to (3-XVIII$_E$) by conventional methods for purification, such as distillation, chromatography, or liquid-liquid extraction. Each of the polyol ethers (3-XVIII$_A$) to (3-XVIII$_E$) may be separately subjected to alkylation, or the mixture of the polyol ethers may be alkylated without separation.

Examples of usable hexahydric alcohols represented by formula (V) are hexitols obtained by reducing hexoses as mentioned above in "(2) A novel method for producing polyol ether derivatives," the hexitol including sorbitol, mannitol, galactitol, iditol, talitol, and allitol.

Usable carbonyl compounds represented by formula (XII) are carbonyl compounds having 2–14 carbon atoms including the carbonyl carbon atom, examples of which are set forth in "(2) A novel method for producing polyol ether derivatives."

The method for producing the polyol ether derivatives as mentioned above in "(2) Novel method for producing polyol ether derivatives" can be employed.

In the hydrogenation reaction, intermediate substances, such as polyol ether ketals and polyol ether acetals, are produced. Examples of such intermediate compounds are represented by the following formulas (3-XIX$_A$) to (3-XIX$_C$), the compounds having one or more ether bonds as well as one or more ketal or acetal rings in a molecule.

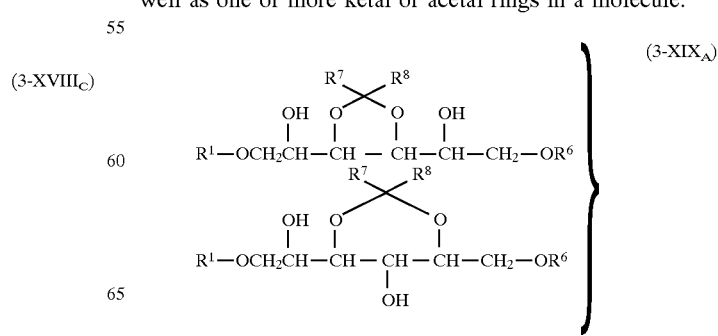

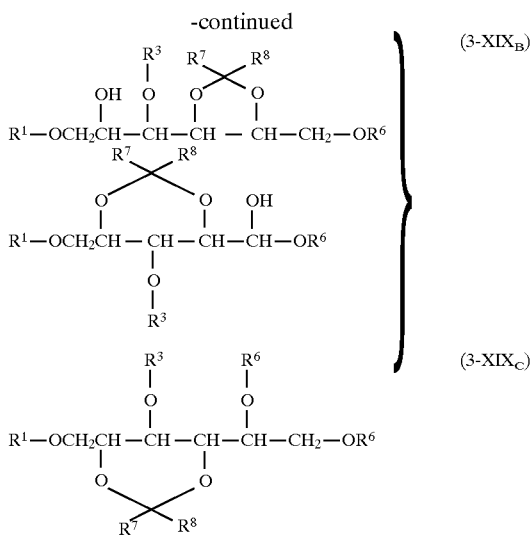

When the polyol ethers (3-XVIII) are obtained as a mixture containing the polyol ether ketals or polyol ether acetals (3-XIX$_A$ to 3-XIX$_C$), the polyol ethers containing no ketal or acetal rings (3XVIII) can be obtained by hydrolysis. Specifically, the mixture obtained is filtered, and volatile materials in the filtrate are evaporated. The residue is then subjected to hydrolysis in a mixed acidic solution consisting of an adequate amount of acid catalyst, such as 0.1 to 1N hydrochloric acid and ethanol.

Also, the mixture of the polyol ethers (3-XVIII) containing those having ketal or acetal rings may be directly subjected to the subsequent alkylation. The polyol ether ketals or polyol ether acetals (3-XIX$_A$ to 3-XIX$_C$) are alkylated to form the ether compounds as represented by formulas (XIII$_{AA}$) and (XIII$_{BB}$).

In formulas (XIII$_{AA}$) and (XIII$_{BB}$), $R^1$ to $R^6$ may be identical or different, each representing a linear alkyl group having 1–14 carbon atoms, a branched alkyl group having 3–14 carbon atoms or a cyclic alkyl group having 3–14 carbon atoms; $R^7$ represents an hydrogen atom, or a linear alkyl group having 1–13 carbon atoms, a branched alkyl group having 3–13 carbon atoms or a cyclic alkyl group having 3–13 carbon atoms; $R^8$ represents a linear alkyl group having 1–13 carbon atoms, a branched alkyl group having 3–13 carbon atoms or a cyclic alkyl group having 3–13 carbon atoms; $R^7$ and $R^8$ may together join to form a ring with an alkylene group having 2–13 carbon atoms; the total number of carbon atoms is 8–40 for $R^1$, $R^2$, $R^3$, $R^6$, $R^7$ and $R^8$ in formula (XIII$_{AA}$), and for $R^1$, $R^4$, $R^5$, $R^6$, $R^7$ and $R^8$ in formula (XIII$_{BB}$), and is 1–13 for $R^7$ and $R^8$ for both formulas; and "a" to "e" are symbols for structure unit, and "a"–"c" or "d"–"e" may be arranged in any sequential order.

The above ether compounds, when used as a base oil for a working fluid composition for a refrigerating machine, give the same effect as the polyol ether derivatives represented by formula (XI), and, therefore, these compounds can be used similarly in a working fluid composition for a refrigerating machine. In such a case, the polyol ether derivatives represented by formula (XIII$_{AA}$) or (XIII$_{BB}$) may be used alone or as a mixture with the polyol ether derivatives represented by formula (XI). When the polyol ether derivatives represented by formula (XIII$_{AA}$) or (XIII$_{BB}$) are used alone, polyol ether acetals or polyol ether ketals separated from a mixture of polyol ethers may be alkylated, or the polyol ether derivatives represented by formula (XIII$_{AA}$) or (XIII$_{BB}$) may be separated from the polyol ether derivatives obtained after alkylation. The methods for separation and alkylation are the same as those for the polyol ether derivatives represented by formula (XI).

The alkyl, alcohol residue, and other groups of the polyol ether derivatives represented by formulas (XIII$_{AA}$) and (XIII$_{BB}$) are the same as those represented by formula (XI).

The thus-obtained polyol ether derivatives represented by formulas (XI) and (XIII$_{AA}$) or (XIII$_{BB}$) may be used after purification to remove by-products or unchanged compounds, or may be used without purification as long as the presence of a small amount of by-products and unchanged compounds does not impair the effects of the present invention. For example, a portion of ketals or acetals (3-XVII) may remain unhydrogenated, and un-capped hydroxyls may also remain.

The polyol ether derivatives represented by formulas (XI) and (XIII$_{AA}$) or (XIII$_{BB}$) and used in the working fluid composition for a refrigerating machine described above in "(3) A working fluid composition for a refrigerating machine comprising a refrigeration oil containing as a base oil polyol ether derivatives and a hydrofluorocarbon" are hereinafter simply referred to as the ether compounds in the present invention) are not particularly restricted in molecular weight. However, when they are used as a refrigeration oil, the average molecular weight is preferably in the range of from 200 to 800, more preferably 300 to 700 in view of better sealing for the compressor, compatibility with hydrofluorocarbon, and lubricity.

The viscosity of the ether compounds in the present invention at 100° C. is preferably 0.5 to 30 mm$^2$/s, more preferably 1 to 15 mm$^2$/s. When the viscosity of the ether compounds in the present invention at 100° C. exceeds 30 mm$^2$/s, the compatibility with hydrofluorocarbons becomes poor. The viscosity at 40° C. of the ether compounds in the present invention is preferably 1 to 300 mm$^2$/s, more preferably 5 to 100 mm$^2$/s. Among the ether compounds in the present invention having a viscosity in the above ranges, preferable are those of which phase separation temperature at low temperature is low. Specifically, suitable examples are those having a critical solution temperature of not higher than 10° C., more preferably not higher than 0° C., further preferably not higher than –10° C.

When used as a refrigeration oil for room air conditioners and refrigerators, the ether compounds in the present invention are required to have good insulating properties. Specifically, the volume resistivity of the ether compounds in the present invention is normally not less than $10^{11}$ Ω·cm, preferably not less than $10^{12}$ Ω·cm, more preferably not less than $10^{13}$ Ω·cm. In order to prevent the solidification of the refrigeration oil at low temperatures, the pour point of the ether compounds in the present invention is preferably not higher than –10° C., more preferably not higher than –20° C.

The refrigeration oil containing the ether compounds in the present invention as a base oil may be a mixture of the ether compounds in the present invention with other synthetic oils, such as mineral oils, poly α-olefins, alkyl benzenes, other ethers and polyethers, PAG, PAG-OH, ketones, esters, perfluoropolyethers, and phosphates. The above-mentioned ether compounds may be used singly or as a mixture of two or more kinds for refrigeration oil containing as a base oil the ether compounds in the present invention.

The ether compounds in the present invention may be used with or without various additives.

For example, room air conditioners are commonly filled with a refrigerant upon installation, and, therefore, there is a high risk of water contamination. Although the ether compounds in the present invention are chemically stable in the presence of water, the insulating materials, such as PET film, may be hydrolyzed in the presence of water to yield PET oligomers, which may result in plugged capillaries of refrigerating machines. Therefore, it is preferred to use additives for removing water, such as epoxy compounds having an epoxy group, orthoesters, acetals (ketals), and carbodiimides.

The refrigeration oil comprising the ether compounds in the present invention which further comprises one or more compounds selected from the group consisting of (a) compounds having an epoxyl group, (b) orthoesters, (c) acetals (ketals), and (d) carbodiimides allows to provide a further improved refrigeration oil, and is an extremely preferable embodiment of the refrigeration oil using as a base oil the ether compounds in the present invention. Accordingly, a working fluid composition for a refrigerating machine comprising such an improved refrigeration oil and a hydrofluorocarbon is an extremely preferable embodiment of the working fluid composition for a refrigerating machine of the present invention.

(a) Compounds having epoxy groups are those having 4–60 carbon atoms, preferably those having 5–25 carbon atoms. Suitable examples include glycidyl ethers, such as phenylglycidyl ether, butylglycidyl ether, 2-ethylhexylglycidyl ether, cresylglycidyl ether, neopentylglycoldiglycidyl ether, 1,6-hexanediol diglycidyl ether, glycerol triglycidyl ether, trimethylolpropane triglycidyl ether, and pentaerythritol tetraglycidyl ether; glycidyl esters, such as diglycidyl phthalate, diglycidyl cyclohexanedicarboxylate, diglycidyl adipate, and glycidyl 2-ethylhexanoate; epoxidated monoesters of fatty acids, such as methyl epoxystearate, and butyl epoxystearate; epoxidated vegetable oils, such as epoxidated soybean oil and epoxidated linseed oil; and alicyclic epoxy compounds, such as epoxycyclooctane, epoxycycloheptane and compounds having an epoxycyclohexyl group and compounds having an epoxycyclopentyl group exemplified below.

The compounds having an epoxycyclohexyl or an epoxycyclopentyl are those having 5 to 40 carbon atoms, preferably 5–25 carbon atoms. Specifically, those set forth in column 11, lines 34 to 46 of Japanese Patent Laid-open No. 5-209171 are suitably used. Though they are not particularly limited, a preference is given to 1,2-epoxycyclohexane, 1,2-epoxycyclopentane, bis(3,4-epoxycyclohexylmethyl) adipate, bis(3,4-epoxy-6-methylcyclohexylmethyl)adipate, 3,4-epoxycyclohexylmethyl-3,4-epoxycyclohexanecarboxylate, and 2-(7-oxabicyclo[4.1.0] hept-3-yl)-spiro(1,3-dioxane-5,3'-[7]oxabicyclo[4.1.0] heptane).

In the present invention, the above epoxy compounds may be used singly or in combination of two or more kinds. The amount of the epoxy compound to be added is usually 0.05 to 2.0 parts by weight, preferably 0.1 to 1.5 parts by weight, more preferably 0.1 to 1.0 parts by weight, based on 100 parts by weight of the ether compounds in the present invention used.

(b) The orthoesters used in the present invention are those having 4–70 carbon atoms, preferably those having 4–50 carbon atoms. Specifically, orthoesters set forth in column 10, lines 7–41 of Japanese Patent Laid-Open No. 6-17073 are suitably used. The amount of orthoesters to be added is normally 0.01 to 100 parts by weight, preferably 0.05 to 30 parts by weight, based upon 100 parts by weight of the ether compounds in the present invention used.

(c) The acetals or ketals added in the present invention are those having 4–70 carbon atoms, preferably those having 4–50 carbon atoms. Specifically, those set forth in column 10, line 47 to column 11, line 21 of Japanese Patent Laid-Open No. 6-17073 are suitably used. The amount of acetals or ketals to be added is normally 0.01 to 100 parts by weight, preferably 0.05 to 30 parts by weight, based upon 100 parts by weight of the ether compounds in the present invention used.

(d) Carbodiimides used in the present invention is represented by the following formula:

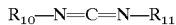

$$R_{10}-N=C=N-R_{11}$$

wherein $R_{10}$ and $R_{11}$ represent a hydrocarbon group having 1–20 carbon atoms, preferably 1–12 carbon atoms; and $R_{10}$ and $R_{11}$ may be identical or different.

Examples of $R_{10}$ and $R_{11}$ include alkyl groups, such as methyl, ethyl, propyl, isopropyl, cyclopropyl, butyl, 1-methylpropyl, 2-methylpropyl, t-butyl, pentyl, 1-methylbutyl, 2-methylbutyl, 3-methylbutyl, 1-ethylpropyl, 1,1-dimethylpropyl, 1,2-dimethylpropyl, 2,2-dimethylpropyl, cyclopentyl, hexyl, 1-methylpentyl, 2-methylpentyl, 3-methylpentyl, 4-methylpentyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethyl-2-methylpropyl, 1-ethyl-1-methylpropyl, 1,1,2-trimethylpropyl, 1,2,2-trimethylpropyl, cyclohexyl, cyclopentylmethyl, methylcyclopentyl, heptyl, 1-methylhexyl, 2-methylhexyl, 3-methylhexyl, 4-methylhexyl, 5-methylhexyl, 1-ethylpentyl, 2-ethylpentyl, 2,4-dimethylpentyl, 3,4-dimethylpentyl, 1,1-dimethylpentyl, 1,4-dimethylpentyl, 1-propylbutyl, 1-isopropylbutyl, 1,3,3-trimethylbutyl, 1,1-diethylpropyl, 2,2-dimethyl-1-ethylpropyl, 1,2-dimethyl-1-ethylpropyl, 1-isopropyl-2-methylpropyl, cycloheptyl, cyclohexylmethyl, methylcyclohexyl, octyl, 1-methylheptyl, 2-methylheptyl, 1-ethylhexyl, 2-ethylhexyl, 1,1,3,3-tetramethylbutyl, 1,1-diisopropylethyl, 1-ethyl-1,2,2-trimethylpropyl, 1,5-dimethylhexyl, 3,5-dimethylhexyl, 2-propylpentyl, 2,4,4-trimethylpentyl, 1-ethyl-2-methylpentyl, 2,2-dimethylhexyl, 1,1-dimethylhexyl, cycloheptylmethyl, dimethylcyclohexyl, 4-methylcyclohexylmethyl, cycloheptylmethyl, cyclooctyl, 1-cyclohexylethyl, 2-cyclohexylethyl, ethylcyclohexyl, nonyl, 1-methyloctyl, 5-methyloctyl, 1-(2'-methylpropyl)-3-methylbutyl, 3,5,5-trimethylhexyl, 1,1-2,2-dimethylpropyl, 3-cyclohexylpropyl, 1,1-dimethylheptyl, decyl, 1-methylnonyl, 1-propylheptyl, 3,7-dimethyloctyl, 2,4,6-trimethylheptyl, 4-cyclohexylbutyl, butylcyclohexyl, 3,3,5,5-tetramethylcyclohexyl, undecyl, 1-methyldecyl, 2-methyldecyl, 2-ethylnonyl, dodecyl, 1-methylundecyl, 2-methylundecyl, 2-ethyldecyl, 1-(2'-methylpropyl)-3,5-dimethylhexyl, tridecyl, 2,4,6,8-tetramethylnonyl, 2-methyldodecyl, 2-ethylundecyl, 1-(3'-methylbutyl)-6-methylheptyl, 1-(1'-methylbutyl)-4-methylheptyl, tetradecyl, 1-methyltridecyl, 2-methyltridecyl, 2-ethyldodecyl, 2-(3'-methylbutyl)-7-methyloctyl, 2-1'-methylbutyl)-5-methyloctyl, pentadecyl, 1-hexylnonyl, 2-methyltetradecyl, 2-ethyltridecyl, hexadecyl, 1-methylpentadecyl, 2-hexyldecyl, heptadecyl, 1-heptyldecyl, 1-(1',3',3'-trimethylbutyl)-4,6,6-trimethylheptyl, 1-(3'-methylhexyl)-6-methylnonyl, octadecyl, 2-heptylundecyl, 2-(1',3',3'-trimethylbutyl)-5,7,7-trimethyloctyl, 2-(3'-methylhexyl)-7-methyldecyl, and 2-octyldodecyl; aryl and alkyl aryl groups, such as phenyl, 2-, 3-, or 4-methylphenyl, 2-, 3-, or 4-ethylphenyl, 2,3-, 2,4-, 2,5-, 2,6-, 3,4-, or 3,5-dimethylphenyl, 2-, 3-, or 4-isopropylphenyl, 2-, 3-, or 4-propylphenyl, 2,3,5-, 2,3,6-, 2,4,6-, or 3,4,5-trimethylphenyl, 2-, 3-, or 4-tert-butylphenyl, 2-, 3-, or 4-sec-butylphenyl, 4- or 5-isopropyl-3-methylphenyl, 4-tert-amylphenyl, 3-, 4-, or 5-methyl-2-tert-butylphenyl, pentamethylphenyl, naphthyl, 2-methylnaphthyl, 2,6-diisopropylphenyl, 4-tert-octylphenyl, 2,4-, 2,6-, or 3,5-di-tert-butylphenyl, di-sec-butylphenyl, 2,6,-di-tert-butyl-4-methylphenyl, and 2,4,6-tri-tert-butylphenyl; and aralkyl groups, such as benzyl, 2-, 3-, or 4-methylbenzyl, phenetyl, sec-phenetyl, 2,4-, 2,5-, 3,4- or 3,5-dimethylbenzyl, 4-ethylbenzyl, 2-, 3-, or 4-methylphenetyl, α- or β-methylphenetyl, α,α-dimethylbenzyl, 1- or 3-phenylpropyl, α- or β-ethylphenetyl, 4-isopropylbenzyl, α-isopropylbenzyl, α,α-dimethylphenetyl, 1-, 3-, or 4-phenylbutyl, α-ethyl-α-methylbenzyl, 4-butylbenzyl, 4-tert-butylbenzyl, 1,1-dimethyl-3-phenylpropyl, 1- or 3-phenyl-2,2-dimethylpropyl, α-propylphenetyl, 5-phenylpentyl, naphthylmethyl, naphthylethyl, and 6-phenylhexyl.

Examples of the carbodiimides include 1,3-diisopropylcarbodiimide, 1,3-di-tert-butylcarbodiimide, 1,3-dicyclohexylcarbodiimide, 1,3-di-p-tolylcarbodiimide, and 1,3-(2,6-diisopropylphenyl)carbodiimide, with a preference given to 1,3-dicyclohexylcarbodiimide, 1,3-di-p-tolylcarbodiimide, and 1,3-bis-(2,6-diisopropylphenyl) carbodiimide.

The amount of the carbodiimide added in the present invention is normally 0.01 to 10 parts by weight, preferably 0.05 to 5 parts by weight, based upon 100 parts by weight of the ether compounds in the present invention.

In addition to the above additive to remove water, the following additives may be added: lubricity additives, such as triaryl phosphate and/or triaryl phosphite; radical trapping additives, such as phenol compounds or metal deactivators having chelating capacity for improving thermal stability; and metal surface protective agents, such as benzotriazol and/or benzotriazol derivatives.

Triaryl phosphates and triaryl phosphites used in the present invention are those having 18–70 carbon atoms, preferably 18–50 carbon atoms. Examples of the triaryl phosphates and triaryl phosphates used in the present invention are set forth in Japanese Patent Laid-Open No. 5-209171, column 12, lines 26 to 41. Among the examples, the following compounds are particularly preferable: triphenyl phosphate, tricresyl phosphate, trixylenyl phosphate, tris(2,4-di-tert-butylphenyl) phosphate, triphenyl phophite, tricresyl phosphite, trixylenyl phosphite, and tris(2,4-di-tert-butylphenyl) phosphite.

The amount of triaryl phosphates and triaryl phosphites added in the present invention is normally 0.1 to 5.0 parts by weight, preferably 0.5 to 2.0 parts by weight, based upon 100 parts by weight of the ether compounds in the present invention.

Phenol compounds having a radical trapping capacity are those having 6–100 carbon atoms, preferably 10–80 carbon atoms. Examples of the phenol compounds are set forth in Japanese Patent Laid-Open No. 5-209171, column 12, line 32 to column 13, line 18. Of the examples, the following compounds are particularly preferable: 2,6-di-tert-butylphenol, 2,6-di-tert-butyl-4-methylphenol, 4,4'-methylenebis(2,6-di-tert-butylphenol), 4,4'-butylidenebis(3-methyl-6-tert-butylphenol), 2,2'-methylenebis(4-ethyl-6-tert-butylphenol), 2,2'-methylenebis(4-methyl-6-tert-butylphenol), 4,4'-isopropylidenebisphenol, 2,4-dimethyl-6-tert-butylphenol, tetrakis[methylene-3-(3,5-di-tert-butyl-4-hydroxyphenyl)propionate]methane, 1,1,3-tris(2-methyl-4-hydroxy-5-tert-butylphenyl)butane, 1,3,5-trimethyl-2,4,6-tris(3,5-di-tert-butyl-4-hydroxybenzyl)benzene, 2,6-di-tert-butyl-4-ethylphenol, 2,6-bis(2'-hydroxy-3'-tert-butyl-5'-methylbenzyl)-4-methylphenol, bis[2-(2-hydroxy-5-methyl-3-tert-butylbenzyl)-4-methyl-6-tert-butylphenyl] terephthalate, triethyleneglycol-bis[3-(3,5-di-tert-butyl-5-methyl-4-hydroxyphenyl)propionate], and 1,6-hexanediol-bis[3-(3,5-di-tert-butyl-4-hydroxyphenyl) propionate].

The amount of the phenol compounds added in the present invention is normally 0.05 to 2.0 parts by weight, preferably 0.05 to 0.5 parts by weight, based upon 100 parts by weight of the ether compounds in the present invention.

The metal deactivators used in the present invention is preferably those with a chelating capacity, and having 5–50 carbon atoms, preferably 5–20 carbon atoms. Examples of the metal deactivators are set forth in Japanese Patent Laid Open No. 5-209171, column 13, line 38 to column 14, line 8. Of the examples, the following compounds are particularly preferable: N,N'-disalicylidene-1,2-diaminoethane, N,N'-disalicylidene-1,2-diaminopropane, acetylacetone, acetoacetate, alizarine, and quinizarin.

The amount of the metal deactivators added in the present invention is normally 0.001 to 2.0 parts by weight, preferably 0.003 to 0.5 parts by weight, based upon 100 parts by weight of the ether compounds in the present invention.

The benzotriazol and benzotriazol derivatives used in the present invention is preferably those having 6–50 carbon atoms, more preferably 6–30 carbon atoms. Examples of the benzotriazol and benzotriazol derivatives are set forth in Japanese Patent Laid Open No. 5-209171, column 13, lines 9 to 29. Of the examples, benzotriazol and 5-methyl-1H-benzotriazol are particularly preferable.

The amount of benzotriazol and/or benzotriazol derivatives added in the present invention is normally 0.001 to 0.1 parts by weight, preferably 0.003 to 0.03 parts by weight, based upon 100 parts by weight of the ether compounds in the present invention.

Other additives conventionally used for lubricating oil, such as antioxidants, extreme pressure additives, oiliness improvers, and defoaming agents, may be added according to necessity. For examples, antioxidants usable in the present invention are amine-based antioxidants, such as p,p-dioctylphenylamine, monooctyldiphenylamine, phenothiazine, 3,7-dioctylphenothiazine, phenyl-1-naphthylamine, phenyl-2-naphthylamine, alkylphenyl-1-naphthylamine, and alkylphenyl-2-naphthylamine; sulfur-based antioxidants, such as alkyl disulfides, thiodipropionic acid esters, and benzothiazoles; and zinc compounds, such as zinc dialkyl dithiophosphate and zinc diaryl dithiophosphate. The amounts of the above additives are 0.05 to 2.0 parts by weight, based on 100 parts by weight of the ether compounds in the present invention.

Examples of the extreme-pressure additives and oiliness agents usable in the present invention are zinc compounds, such as zinc dialkyl dithiophosphate and zinc diaryl dithiophosphate; sulfur compounds, such as thiodipropionic acid esters, dialkyl sulfide, dibenzyl sulfide, dialkyl polysulfide, alkyl mercaptan, dibenzothiophene, and 2,2'-dithiobis (benzothiazole): phosphorus compounds, such as trialkyl phosphite, and trialkyl phosphate; chlorine compounds, such as chlorinated paraffin; molybdenum compounds, such as molybdenum dithiocarbamate, molybdenum dithiophosphate, and molybdenum disulfide; fluorine compounds, such as perfluoroalkyl polyethers, trifluorochloro ethylene polymers, graphitefluoride; silica compounds, such as fatty acid-modified silicone; and graphite. The amount added in the present invention is 0.05 to 10 parts by weight, based upon 100 parts by weight of the ether compound of the present invention.

Examples of defoaming agents usable in the present invention are silicone oils, such as dimethylpolysiloxane; and organosilicates, such as diethyl silicate. The amount added in the present invention is 0.0005 to 1 parts by weight, based on 100 parts by weight of the ether compound of the present invention.

Additives stabilizing freon refrigerants, such as organic tin compounds and boron compounds, may be added in the present invention. The amount added in the present invention is 0.001 to 10 parts by weight, based on 100 parts by weight of the ether compounds in the present invention.

The mixing ratio of a hydrofluorocarbon with a refrigeration oil containing the ether compounds in the present invention as a base oil or with a refrigeration oil containing the above base oil to which additives are further added (hydrofluorocarbon/oil) is normally 50/1 to 1/20 (weight ratio), preferably 10/1 to 1/5 (weight ratio). When the mixing ratio exceeds 50/1, the viscosity of the mixed solution of hydrofluorocarbon and oil becomes low, thereby making it likely to have undesirably poor lubricity. When the mixing ratio is lower than 1/20, the refrigeration ability is likely to become undesirably poor.

The hydrofluorocarbons used in the present invention include difluoromethane (HFC32), 1,1-difluoroethane (HFC152a), 1,1,1-trifluoroethane (HFC143a), 1,1,1,2-tetrafluoroethane (HFC134a), 1,1,2,2-tetrafluoroethane (HFC134) and pentafluoroethane (HFC125), with a particular preference given to 1,1,1,2-tetrafluoroethane, pentafluoroethane, and difluoromethane.

EXAMPLES

The present invention will be further described by means of Examples, without intending to restrict the scope of the present invention thereto.

Example 1-1

Synthesis of 1,6-di-O-(3,5,5-trimethylhexyl)sorbitol [Compound (1b)]

1) 1.2:3.4:5.6-tri-O-(3,5,5-trimethylhexylidene)sorbitol: Compound (1a)

In a 3-liter reaction vessel equipped with a thermometer, a reflux condenser, a Dean and Stark trap, a calcium chloride tube, and a stirrer, 170.76 g (0.937 mol) of D-sorbitol, 400 g (2.812 mol) of 3,5,5-trimethylhexanal, 1.78 g (0.00936 mol) of p-toluene sulfonic acid 1 hydrate, and 400 ml of hexane were placed and heated with stirring. A reaction was carried out at a temperature of from 79° to 81° C. for 8 hours while distilling off a theoretical amount of water. After being cooled to 70° C., the reaction mixture was neutralized by adding 1.99 g (0.0188 mol) of sodium carbonate, and stirred at 70° C. for 30 minutes. After 100 g of water was added to the mixture and stirred at 60° C. for 30 minutes, the mixture was allowed to stand to separate into two layers. After the lower layer was discarded, the remaining mixture was washed with 100 g of saturated brine, and evaporated to give 529.51 g of crude Compound (1a).

The obtained product was subjected to a reduced-pressure distillation and a forerun was discarded. 500.87 g of the residue was dissolved in 500 ml of hexane. The hexane solution was subjected to an adsorption treatment by passing through 25.04 g (5% by weight to the residue) of activated clay on a filter (PTFE, 0.2 μm) under pressure. After washing the clay cake with hexane, the hexane in the solution was completely distilled away to give 501.14 g of Compound (1a) (yield: 96.4%).

The product has a purity of 96.3% as determined by gas chromatography, and a hydroxyl value of 27.2 (theoretical value of 0).

2) 1,6-di-O-(3,5,5-trimethylhexyl)sorbitol: Compound (1b)

In a 1-liter autoclave, 487.1 g (0.878 mol) of the obtained Compound (1a), and 9.74 g (2% by weight) of 5% Pd/C catalyst were placed, the 5% Pd/C catalyst being prepared by drying a commercially available product with 50% moisture content (5% Pd carbon powder with 50% moisture content, E-type, pH 6.0, manufactured by N. E. Chemcat Corp.) at room temperature for one day under reduced pressure using a vacuum pump. The temperature of the autoclave was raised with stirring the mixture under a hydrogen pressure of 20 kg/cm². Then the mixture was kept for 8 hours under a hydrogen pressure of 200 kg/cm² at 190° C. The hydroxyl value at the completion of the reaction was 243.3 [theoretical value: 300.9 (as an ether alcohol with an average alkyl substituent number of 3.0)]. The reaction mixture was dissolved in 300 ml of isopropanol, and the mixture was subjected to a pressure-filtration through a membrane filter (PTFE, 0.2 μm). The filtrate was evaporated to give 475.85 g of a crude mixture of polyol ethers (yield of crude mixture: 96.6%). The composition of the mixture determined by gas chromatography was as follows: 19% of dialkyl product; 47% of trialkyl product; 18% of tetraalkyl product; 3% of monoalkyl product; and 2% of pentaalkyl product. 200 g of the crude mixture was weighed and subjected to a silica gel column chromatography for purification, in which 18.2 g of purified Compound (1b) was obtained by elution with hexane/ethanol [93/7 (vol/vol)] after elution of Compound (3) with hexane/ethanol [97/3 (vol/vol)] and elution of Compound (2) with hexane/ethanol [95/5 (vol/vol)]. The purity of Compound (1b) was determined to be 90.5% by gas chromatography, and the hydroxyl value of the compound was 471 (theoretical value: 517).

IR (NEAT, cm$^{-1}$):
3465 (O—H stretching), 2954 (C—H stretching), 1473, 1395, 1368 (C—H deformation), 1122 (C—O stretching)
$^1$H NMR (CDCl$_3$, δ ppm):
0.77–1.35 (28H, multiplet, —CH(C$\underline{H}_3$)CH$_2$C(C$\underline{H}_3$)$_3$)
1.35–1.75 (2H, multiplet, —C$\underline{H}_2$CH(CH$_3$)CH$_2$C(CH$_3$)$_3$)
3.03 (4H, singlet, —O$\underline{H}$)
3.43–4.02 (12H, multiplet, —C$\underline{H}$(OH)—, —C$\underline{H}_2$OC$\underline{H}_2$—)
MASS (FD):436 (M+1)

Example 1-2

Synthesis of 1,3,6-tri-O-(3,5,5-trimethylhexyl) sorbitol [Compound (2)]

100 g of the crude mixture of polyol ethers obtained in Example 1-1 was purified similarly to Example 1-1 by silica gel column chromatography. That is, after Compound (3) was eluted with hexane/ethanol [97/3 (vol/vol)], Compound (2) was eluted using a hexane/ethanol [95/5 (vol/vol)] developing solvent. As a result, 32.3 g of Compound (2) was obtained. The purity of Compound (2) was determined to be 93.3% by gas chromatography, and the hydroxyl value of the compound was 280 (theoretical value: 301).

IR (NEAT, cm$^{-1}$):
3466 (O—H stretching), 2956 (C—H stretching), 1473, 1395, 1368 (C—H deformation), 1122 (C—O stretching)
$^1$H NMR (CDCl$_3$, δ ppm):
0.77–1.35 (42H, multiplet, —CH(C$\underline{H}_3$)CH$_2$C(C$\underline{H}_3$)$_3$)
1.35–1.80 (9H, multiplet, —C$\underline{H}_2$CH(CH$_3$)CH$_2$C(CH$_3$)$_3$)
3.40–4.00 (14H, multiplet, —C$\underline{H}$(OH)—, —C$\underline{H}_2$OC$\underline{H}_2$—)
MASS (FD): 688 (M+1)

Example 1-3

Synthesis of 1,3,6,x-tetra-O-(3,5,5-trimethylhexyl) sorbitol [Compound (3)]
(x represents a figure of 2, 4 or 5; x in the Examples below has the same definition)

100 g of the crude mixture of polyol ethers obtained in Example 1-1 was purified similarly to Example 1-1 by silica gel column chromatography using a hexane/ethanol [97/3 (vol/vol)] developing solvent to give 24.0 g of Compound (3). The purity of Compound (3) was determined to be 83.5% by gas chromatography, and the hydroxyl value of the compound was 174 (theoretical value: 163).

IR (NEAT, cm$^{-1}$):
3465 (O—H stretching), 2954 (C—H stretching), 1473, 1394, 1367 (C—H deformation), 1120 (C—O stretching)
MASS (FD):351 (M+1)

Example 1-4

Synthesis of a mixture of 1-O-(3,5,5-trimethylhexyl)sorbitol, 1,6-di-O-(3,5,5-trimethylhexyl)sorbitol, 1,3,6-tri-O-(3,5,5-trimethylhexyl)sorbitol, 1,3,6,x-tetra-O-(3,5,5-trimethylhexyl)sorbitol, and 1,3,6,x,y-penta-O-(3,5,5-trimethylhexyl)sorbitol (ether alcohols having an average alkyl substituent number of 3.1) [Compounds (4)]

(y represents a figure of 2, 4, or 5, the figure being different from x; y in the Examples below has the same definition)

200 g of the crude mixture of polyol ethers obtained in Example 1-1 was purified by heating under a reduced pressure (192° C. at 0.6 mmHg) to remove low-boiling point components. As a result, 178 g of Compounds (4) was obtained (yield: 89.2%). The composition of the obtained Compounds (4) as determined by gas chromatography was as follows: 3% of monoalkyl product; 21% of dialkyl product; 53% of trialkyl product; 20% of tetraalkyl product; and 2% of pentaalkyl product. The hydroxyl value of the mixture was 282 (ether alcohols with an average alkyl substituent number of 3.1).

IR (NEAT, cm$^{-1}$):
3466 (O—H stretching), 2955 (C—H stretching), 1473, 1395, 1367 (C—H deformation), 1118 (C—O stretching)

Example 1-5

Synthesis of a mixture of 1-mono-O-(3,5,5-trimethylhexyl)sorbitol, 1,6-di-O-(3,5,5-trimethylhexyl)sorbitol, 1,3,6-tri-O-(3,5,5-trimethylhexyl)sorbitol, 1,3,6,x-tetra-O-(3,5,5-trimethylhexyl)sorbitol, and 1,3,6,x,y-penta-O-(3,5,5-trimethylhexyl)sorbitol (ether alcohols having an average alkyl substituent number of 2.0) [Compounds (5)]

In a 1-liter autoclave, 480 g (0.865 mol) of 1.2:3.4:5.6-tri-O-(3,5,5-trimethylhexylidene)sorbitol (1a), 78.8 g (0.433 mol) of D-sorbitol, and 9.74 g (2% by weight) of 5% Pd/C catalyst were placed, the 5% Pd/C catalyst being prepared by drying a commercially available product with 50% moisture content (5% Pd carbon powder with 50% moisture content, E-type, pH 6.0, manufactured by N. E. Chemcat Corp.) at room temperature for one day under a reduced pressure using a vacuum pump. The temperature of the autoclave was raised with stirring the mixture under a hydrogen pressure of 20 kg/cm$^2$. Then the mixture was kept for 25 hours under a hydrogen pressure of 200 kg/cm$^2$ at 190° C. The reaction mixture was dissolved in 300 ml of isopropanol, and subjected to a pressure-filtration through a membrane filter (PTFE, 0.2 μm). The filtrate was evaporated to give 532.0 g of a crude mixture of polyol ethers (yield of crude mixture: 95.1%).

The crude mixture of polyol ethers obtained was purified by heating under a reduced pressure (182°–207° C. at 0.6 mmHg) to remove low-boiling point components. As a result, 484 g of Compounds (5) was obtained (yield: 91.0%).

The composition of the obtained Compounds (5) as determined by gas chromatography was as follows: 34% of monoalkyl product; 47% of dialkyl product; 16% of trialkyl product; and 1% of tetraalkyl product. The hydroxyl value of the mixture was 521 (ether alcohols with an average alkyl substituent number of 2.0).

Example 1-6

Synthesis of 2,3,4,5-tetra-O-methyl-1,6-di-O-(3,5,5-trimethylhexyl)sorbitol [Compound (6)]

In a 1-liter reaction vessel equipped with a thermometer, a reflux condenser, a dropping funnel, and a stirrer, 7.3 g (0.18 mol) of sodium hydride (content:60%, oily) was placed. The sodium hydride was washed with 50 ml of hexane by decantation. Then, 320 ml of a mixed solvent of 1,2-dimethoxyethane/dimethylsulfoxide (3/1, vol/vol) was added to the vessel. Then, 17.0 g (0.039 mol) of Compound (1b) obtained in Example 1-1 was dissolved in 16 ml of the mixed solvent and added dropwise to the vessel with stirring over 10 minutes at room temperature. The reaction mixture was heated to 50° C., and stirred for 1 hours with maintaining the temperature. After the mixture was cooled to 40° C., 22.9 g (0.18 mol) of dimethyl sulfate was added dropwise over 20 minutes with the temperature maintained below 50° C. After the mixture was stirred for another 1 hour at 50° C. and cooled, 72.0 g (0.18 mol) of 10% aqueous solution of sodium hydroxide was added. Then the mixture was stirred at 70° to 80° C. for 1 hour. After cooling, 100 ml of water was added to allow phase separation. The aqueous layer was extracted twice with 150 ml of diethyl ether, and the organic layer was combined with the ether extracts. The mixture was washed three times with 100 ml of saturated brine and dried over anhydrous sodium sulfate. Then, the solvent was distilled away with an evaporator to give 21.2 g of oily substance. This substance was purified by silica gel column chromatography using a hexane/diethyl ether [90/10 (vol/vol)] developing solvent and subjected to a reduced-pressure distillation (boiling point: 179° C. at 0.35 mmHg) to give 6.8 g of Compound (6). The purity of Compound (6) was determined to be 99.7% by gas chromatography.

IR (NEAT, cm$^{-1}$):
2950 (C—H stretching), 1473, 1368 (C—H deformation), 1116 (C—H stretching)
$^1$H NMR (CDCl$_3$, δ ppm):
0.80–1.33 (28H, multiplet, —CH(C$\underline{H}_3$)CH$_2$C(C$\underline{H}_3$)$_3$)
1.33–1.80 (6H, multiplet, —C$\underline{H}_2$C$\underline{H}$(CH$_3$)CH$_2$C(CH$_3$)$_3$)
3.35–3.80 (24H, multiplet, —C$\underline{H}$(OC$\underline{H}_3$)—, —C$\underline{H}_2$OC$\underline{H}_2$—)

Example 1-7

Synthesis of 2,4,5-tri-O-methyl-1,3,6-tri-O-(3,5,5-trimethylhexyl)sorbitol [Compound (7)]

In a 1-liter reaction vessel equipped with a thermometer, a reflux condenser, a dropping funnel, and a stirrer, 4.9 g (0.12 mol) of sodium hydride (content:60%, oily) was placed. The sodium hydride was washed with 50 ml of hexane by decantation. Then, 320 ml of a mixed solvent of 1,2-dimethoxyethane/dimethylsulfoxide (3/1, vol/vol) was added to the vessel. 15.3 g (0.027 mol) of Compound (2) obtained in Example 1-2 was dissolved in 12 ml of the mixed solvent and added dropwise to the vessel with stirring over 10 minutes at room temperature. The reaction mixture was heated to 50° C. and stirred for 30 minutes with maintaining the temperature. After the mixture was cooled to 40° C., 15.5 g (0.12 mol) of dimethyl sulfate was added dropwise over 1 hour with the temperature maintained below 50° C. After the mixture was stirred for another 1 hour at 50° C. and cooled, 48.0 g (0.12 mol) of 10% aqueous solution of sodium hydroxide was added. Then the mixture was stirred at 70° to 80° C. for 1 hour. After cooling, the mixture was allowed to phase separate. The aqueous layer was extracted twice with 100 ml of diethyl ether, and then the organic layer was combined with the ether extracts. The mixture was washed three times with 50 ml of saturated brine and dried over anhydrous sodium sulfate. Then, the solvent was distilled away with an evaporator to give 16.9 g of oily substance. This substance was purified by silica gel column chromatography using a hexane/diethyl ether [90/10 (vol/vol)] developing solvent to give 12.6 g of Compound (7). The purity of Compound (7) was determined to be 98.4% by gas chromatography.

IR (NEAT, cm$^{-1}$):
2956 (C—H stretching), 1470, 1368 (C—H deformation), 1194 (C—O stretching)
$^1$H NMR (CDCl$_3$, δ ppm):
0.78–1.10 (42H, multiplet, —CH(C$\underline{H}_3$)CH$_2$C(C$\underline{H}_3$)$_3$)
1.16–1.78 (9H, multiplet, —C$\underline{H}_2$C$\underline{H}$(CH$_3$)CH$_2$C(CH$_3$)$_3$)
3.23–3.85 (23H, multiplet, —C$\underline{H}$(OC$\underline{H}_3$)—, —C$\underline{H}_2$OC$\underline{H}_2$—)

Example 1-8-1

Synthesis of a mixture of 2,3,4,5,6-penta-O-methyl-1-O-(3,5,5-trimethylhexyl)sorbitol, 2,3,4,5-tetra-O-methyl-1,6-di-O-(3,5,5-trimethylhexyl)sorbitol, 2,4,5-tri-O-methyl-1,3,6-tri-O-(3,5,5-trimethylhexyl) sorbitol, di-O-methyl-1,3,6,x-tetra-O-(3,5,5-trimethylhexyl)sorbitol, and O-methyl-1,3,6,x,y-penta-O-(3,5,5-trimethylhexyl)sorbitol (methyl-capped ether alcohols having an average alkyl substituent number of 2.0) [Compounds (8-1)]

In a 3-liter reaction vessel equipped with a thermometer, a reflux condenser, a dropping funnel, and a stirrer, 117 g (3.06 mol) of sodium hydride (content:60%, oily) was placed. The sodium hydride was washed with 400 ml of hexane by decantation. Then, 1.5 liters of toluene was added to the vessel.

220 g of Compounds (5) obtained in the same way as in Example 1-5 (ether alcohol with hydroxyl value of 521 and average alkyl substituent number of 2.0), i.e., a mixture of mono-, di-, tri-, tetra-, and penta-O-(3,5,5-trimethylhexyl) sorbitol, was dissolved in 300 ml of toluene, and added dropwise to the vessel over 30 minutes at 24° to 36° C. The reaction mixture was heated to 90° to 97° C. and stirred for 30 minutes with maintaining the temperature. After the mixture was cooled to 40° C., 386 g (3.06 mol) of dimethyl sulfate was added dropwise over 2.5 hours with the temperature maintained below 60° C. After the mixture was stirred for another 1 hour at 60° C. and cooled, 898 g (3.37 mol) of 15% aqueous solution of sodium hydroxide was added. Then the mixture was stirred at. 80° C. for 1 hour. After cooling, the mixture was allowed to phase separate. The water layer was extracted once with 300 ml of toluene, and the organic layer was combined with the toluene. The mixture was washed three times with 40 ml of saturated brine. Then, the mixture was dried over anhydrous sodium sulfate, and the solvent was distilled away with an evaporator to give 248 g of oily substance. The substance was purified by heating at 185° to 190° C. under a reduced pressure (0.7 mmHg) for 30 minutes to remove low-boiling point components. As a result 226 g of Compounds (8-1) was obtained. The composition of the obtained Compounds (8-1) as determined by gas chromatography was as follows: 34% of monoalkyl product; 47% of dialkyl product; 16% of trialkyl product; and 1% of tetraalkyl product.

IR (NEAT, cm$^{-1}$):
2956 (C—H stretching), 1473, 1368 (C—H deformation), 1104 (C—O stretching)

Example 1-8-2

Synthesis of a mixture of 2,3,4,5-tetra-O-methyl-1,6-di-O-(3,5,5-trimethylhexyl)sorbitol, 2,4,5-tri-O-methyl-1,3,6-tri-O-(3,5,5-trimethylhexyl)sorbitol, di-O-methyl-1,3,6,x-tetra-O-(3,5,5-trimethylhexyl) sorbitol, and 2,3,4,5,6-penta-O-methyl-1-O-(3,5,5-trimethylhexyl)sorbitol (methyl-capped ether alcohols having an average alkyl substituent number of 3.1) [Compounds (8-2)]

In a 2-liter reaction vessel equipped with a thermometer, a reflux condenser, a dropping funnel, and a stirrer, 25.35 g (1.06 mol) of sodium hydride powder and 500 ml of toluene were placed. 100 g (0.2 mol) of Compounds (4) obtained in the same way as in Example 1-4, i.e., a mixture of mono-, di-, tri-, and tetra-O-(3,5,5-trimethylhexyl)sorbitol, was dissolved in 100 ml of toluene, and added dropwise to the vessel over 30 minutes with stirring at room temperature under nitrogen atmosphere. Then, 200 ml of toluene was added to the vessel. The reaction mixture was heated to 110° C. and refluxed with stirring for 30 minutes at 110° C. After the mixture was cooled to 50° C., 133.22 g (1.06 mol) of dimethyl sulfate was added dropwise over 1 hour with the temperature maintained below 50° C. 600 ml of toluene was further added and the mixture was matured for 1 hour at 80° C. After the mixture was cooled and 422.5 g of 10% aqueous solution (1.06 mol) of sodium hydroxide was added, the mixture was stirred at 70° to 80° C. for 30 minutes. After being cooled to room temperature, the mixture was allowed to phase separate. The lower layer was discarded. The upper layer was washed four times with 200 ml of saturated brine. Then, the mixture was dried over anhydrous sodium sulfate, and subjected to adsorption treatment with 2.2 g of activated carbon (2% by weight of activated carbon based on the theoretical yield). After filtration, toluene in the filtrate was distilled away to give oily substance. The oily substance was further heated under a reduced pressure of 0.7 mmHg and the forerun was discarded until the internal temperature reached 200° C. As a result, 70.4 g of Compounds (8-2) was obtained (yield: 64.4%).

The purity of the Compounds (8-2) was determined to be 96.1% by gas chromatography.

The composition of the mixture was as follows: 3.5% by weight of 2,3,4,5,6-penta-O-methyl-1-O-(3,5,5-trimethylhexyl)sorbitol; 37.6% by weight of 2,3,4,5-tetra-O-methyl-1,6-di-O-(3,5,5-trimethylhexyl)sorbitol; 42.9% by weight of 2,4,5-tri-O-methyl-1,3,6-tri-O-(3,5,5-trimethylhexyl)sorbitol; and 12.1% by weight of di-O-methyl-1,3,6,x-tetra-O-(3,5,5-trimethylhexyl)sorbitol.

Example 1-9

Synthesis of 1,6-di-O-(1-methylpropyl)-O-(1-methylpropylidene)sorbitol [Compound (9b)]
1) 1.2:3.4:5.6-tri-O-(1-methylpropylidene)sorbitol: Compound (9a)

In a 3-liter reaction vessel equipped with a thermometer, a reflux condenser, a Dean and Stark trap, a calcium chloride tube, and a stirrer, 336.84 g (1.849 mol) of D-sorbitol, 800 g (11.094 mol) of methyl ethyl ketone, 17.58 g (0.092 mol) of p-toluene sulfonic acid 1 hydrate, and 200 ml of hexane were placed and heated with stirring. A reaction was carried out at a temperature of from 69° to 79° C. for 8 hours while distilling off a theoretical amount of water. After being cooled to 60° C., the reaction mixture was neutralized by adding 19.60 g (0.185 mol) of sodium carbonate, and stirred at 60° C. for 30 minutes. After 200 g of water was added to the mixture and stirred at 60° C. for 30 minutes, the mixture was allowed to stand to separate into two layers. After the lower layer was discarded, the remaining mixture was washed with 200 g of saturated brine, and evaporated to give 643.75 g of crude Compound (9a). The crude compound was subjected to a reduced-pressure distillation to give 606.71 g of Compound (9a) (yield: 95.3%). The obtained Compound (9a) had a boiling point of 136° to 140° C. at 0.6 mmHg, purity as determined by gas chromatography of 97.3%, and a hydroxyl value of 12.9 (theoretical value:0).

2) 1,6-di-O-(1-methylpropyl)-O-(1-methylpropylidene) sorbitol: Compound (9b)

In a 1-liter autoclave, 571.5 g (1.659 mol) of Compound (9a) obtained above, and 11.43 g (2% by weight) of 5% Pd/C catalyst were placed, the 5% Pd/C catalyst being prepared by drying a commercially available product with 50% moisture content (5% Pd carbon powder with 50.0% moisture content, E-type, pH 6.0, manufactured by N. E. Chemcat Corp.) at room temperature for one day under a reduced pressure using a vacuum pump. The temperature of the autoclave was raised with stirring the mixture under a hydrogen pressure of 20 kg/cm$^2$. Then the mixture was kept for 15 hours under a hydrogen pressure of 200 kg/cm$^2$ with the heating maintained at 190° C. The hydroxyl value at the completion of the reaction was 403.5 [theoretical value: 480.23 (as an ether alcohol with an average alkyl substituent number of 3.0)]. The reaction mixture was dissolved in 200 ml of isopropanol, and the mixture was subjected to a pressure-filtration through a membrane filter (PTFE, 0.2 μm). The filtrate was evaporated to give 551.34 g of a crude Compound (9b) (yield of crude compound: 96.5%). The composition of the crude compound determined by gas chromatography was as follows: 16% of dialkyl ether; 20% of trialkyl ether; 51% of dialkyl ether monoketal; 10% of trialkyl ether monoketal; and 1% of tetraalkyl ether. 500 g of the crude compound was dissolved in 500 ml of hexane, which was washed three times with methanol/water (200 ml/200 ml), three times with methanol/water (200 ml/100 ml), and four times with methanol/water (100 ml/100 ml). The upper hexane layer obtained was evaporated to give 251.84 g of partially purified hydrogenated compound.

The obtained compound was dissolved in 250 ml of hexane and purified by silica gel column chromatography. The fractions eluted with hexane/ethanol (99/1) were collected and evaporated to give 131.92 g of Compound (9b). The obtained Compound (9b) has a purity of 97.7% as determined by gas chromatography, and a hydroxyl value of 327.5 (theoretical value: 322.01).

IR (NEAT, cm$^{-1}$):
3492 (O—H stretching), 2972, 2936, 2884 (C—H stretching), 1468, 1378 (C—H deformation), 1082 (C—O stretching)

$^1$H NMR (CDCl$_3$, δ ppm):
0.92 (9H, triplet, —CH$_2$CH$_3$)
1.12 (6H, doublet, —CH$_2$CH$_3$)
1.38 (3H, singlet, (—O—)$_2$C(CH$_3$)CH$_2$CH$_3$)
1.43–1.80 (6H, multiplet, —CH$_2$CH$_3$)
2.85 (2H, singlet, —OH)
3.29–4.33 (10H, multiplet, —O—CH$_2$—, —O—CH—)
MASS (FD):349 (M+1)

Example 1-10

Synthesis of 1,3,6-tri-O-(1-methylpropyl)sorbitol [Compound (10)]

251.84 g of the partially purified hydrogenated compound obtained in Example 1-9 was dissolved in 250 ml of hexane and purified by silica gel column chromatography. That is, after Compound (9b) was eluted with hexane/ethanol (99/1), fractions eluted with hexane/ethanol (95/5) were collected and evaporated to give 55.42 g of Compound (10). The obtained compound had a purity of 97.3% as determined by gas chromatography and a hydroxyl value of 453.1 (theoretical value of 480.24).

IR (NEAT, cm$^{-1}$):
3464 (O—H stretching), 2972, 2932, 2880 (C—H stretching), 1466, 1380 (C—H deformation), 1086 (C—O stretching)

$^1$H NMR (CDCl$_3$, δ ppm):
0.92 (9H, triplet, —CH$_2$CH$_3$)
1.13 (9H, doublet, —CHCH$_3$)
1.32–1.78 (6H, multiplet, —CH$_2$CH$_3$)
3.13 (3H, broad singlet, —OH)
3.30–4.02 (—O—CH$_2$—, —O—CH—)
MASS(FD): 351 (M+1)

Example 1-11

Synthesis of 1,6-di-O-(1-methylpropyl)-di-O-methyl-O-(1-methylpropylidene)sorbitol [Compound (11)]

In a 1-liter reaction vessel equipped with a thermometer, a reflux condenser, a dropping funnel, and a stirrer, 12.38 g (0.516 mol) of sodium hydride powder and 300 ml of toluene were placed. 70 g (0.201 mol) of Compound (9b) obtained in Example 1-9 was dissolved in 100 ml of toluene, and added dropwise to the vessel over 20 minutes with stirring at room temperature under nitrogen atmosphere. The reaction mixture was heated to 110° C. and refluxed with stirring for 30 minutes. After the mixture was cooled to 50° C., 65.08 g (0.516 mol) of dimethyl sulfate was added dropwise over 1 hour with the temperature maintained at 50° C. The mixture was matured for 1 hour at 80° C. After the mixture was cooled and 206.4 g of 10% aqueous solution (0.516 mol) of sodium hydroxide was added, the mixture was stirred at 70° to 80° C. for 30 minutes. After being cooled to room temperature, the mixture was extracted with 200 ml of ether, washed twice with 100 ml of saturated brine, dried over anhydrous sodium sulfate, and evaporated to give 76.72 g of viscous oily substance. The substance obtained was subjected to a reduced-pressure distillation to give 68.83 g of Compound (11) (yield: 92.1%). The obtained Compound (11) had a boiling point of 127° to 128° C. at 0.4 mmHg, a purity of 99.0% as determined by gas chromatography, and a hydroxyl value of 0.67 (theoretical value: 0).

IR (NEAT, cm$^{-1}$):
2974, 2925 (C—H deformation), 1470, 1377, 1341 (C—H deformation), 1089 (C—O stretching)

$^1$H NMR (CDCl$_3$, δ ppm):
0.90 (9H, triplet, —CH$_2$CH$_3$)
1.10–1.20 (6H, multiplet, —CH(CH$_3$CH$_2$CH$_3$)
1.29–1.42 (3H, multiplet, (—O—)$_2$C(CH$_3$)CH$_2$CH$_3$)
1.42–1.80 (6H, multiplet, —CH$_2$CH$_3$)

3.29–3.80 (14H, multiplet, —C$\underline{H}_2$—O—C$\underline{H}$(CH$_3$)CH$_2$CH$_3$, C$\underline{H}$—O—C$\underline{H}_3$)

Example 1-12

Synthesis of 2,4,5-tri-O-ethyl-1,3,6-tri-O-(1-methylpropyl)sorbitol [Compound (12)]

In a 300-milliliter reaction vessel equipped with a thermometer, a reflux condenser, a dropping funnel, and a stirrer, 3.70 g (0.154 mol) of sodium hydride powder and 100 ml of toluene were placed. 12 g (0.0342 mol) of Compound (10b) obtained in Example 1-10 was dissolved in 50 ml of toluene, and added dropwise to the vessel over 20 minutes with stirring at room temperature under nitrogen atmosphere. The reaction mixture was heated to 110° C. and refluxed with stirring for 30 minutes with maintaining the temperature. After the mixture was cooled to 500° C., 23.75 g (0.154 mol) of dimethyl sulfate was added dropwise over 45 minutes with the temperature maintained at 50° C. The mixture was matured for 2 hours at 80° C. After the mixture was cooled and 61.6 g (0.154 mol) of 10% aqueous solution of sodium hydroxide was added, the mixture was stirred at 70° to 80° C. for 30 minutes. After the mixture was cooled to room temperature, the lower layer was discarded, and the upper toluene layer was washed twice with 50 ml of saturated brine, dried over anhydrous sodium sulfate, and evaporated to give 14.8 g of viscous oily substance. The substance obtained was subjected to a reduced-pressure distillation to give 13.69 g of Compound (12) (yield: 92.0%). The obtained Compound (12) had a boiling point of 145° to 146° C. at 0.5 mmHg, a purity of 96.2% as determined by gas chromatography, and a hydroxyl value of 0.5 (theoretical value: 0).

IR (NEAT, cm$^{-1}$):
2974, 2932, 2878 (C—H stretching), 1467, 1377, 1341 (C—H deformation), 1110 (C—O stretching)

$^1$H NMR (CDCl$_3$, δ ppm):
0.82–1.08 (9H, triplet, —CH(CH$_3$)CH$_2$C$\underline{H}_3$)
1.08–1.80 (24H, multiplet, —CH(C$\underline{H}_3$)C$\underline{H}_2$CH$_3$, —OCH$_2$C$\underline{H}_3$)
3.21–4.00 (17H, multiplet, —C$\underline{H}$—O—C$\underline{H}_2$—, —C$\underline{H}$—OC$\underline{H}$(CH$_3$)—)

Example 1-13

Synthesis of 1,6-di-O-(1,3-dimethylbutyl)-O-(1,3-dimethylbutylidene)sorbitol [Compound (13b)]

1) 1.2:3.4:5.6-tri-O-(1,3-dimethylbutylidene)sorbitol: Compound (13a)

In a 3-liter reaction vessel equipped with a thermometer, a reflux condenser, a Dean and Stark trap, a calcium chloride tube, and a stirrer, 363.76 g (1.997 mol) of D-sorbitol, 1200 g (11.981 mol) of methyl isobutyl ketone, 18.99 g (0.0998 mol) of p-toluene sulfonic acid 1 hydrate, and 300 ml of hexane were placed and heated with stirring. A reaction was carried out at a temperature of from 93° to 98° C. for 23 hours while distilling off a predetermined amount of water. After being cooled to 60° C., the reaction mixture was neutralized by adding 21.16 g (0.1996 mol) of sodium carbonate, and stirred at 60° C. for 30 minutes. After 200 g of water was added to the mixture and stirred at 60° C. for 30 minutes, the mixture was allowed to stand to separate into two layers. After the lower layer was discarded, the remaining mixture was washed with 200 g of saturated brine and evaporated to give 736.65 g of crude Compound (13a). The obtained crude Compound (13a) was subjected to a reduced-pressure distillation and a forerun was discarded. 657.62 of the residue obtained was subjected to an adsorption treatment by passing through 33 g (5% by weight to the residue) of activated clay on a filter (PTFE, 0.2 μm) by a pressure filtration. As a result, 637.44 g of Compound (13a) was obtained (yield: 74.5%).

The purity of Compound (13a) as determined by gas chromatography was 96.1%, and a hydroxyl value was 34.3 (theoretical value:0).

2) 1,6-di-O-(1,3-dimethylbutyl)-O-(1,3-dimethylbutylidene)sorbitol: Compound (13b)

In a 1-liter autoclave, 612 g (1.428 mol) of Compound (13a) obtained above, and 12.24 g (2% by weight) of 5% Pd/C catalyst were placed, the 5% Pd/C catalyst being prepared by drying a commercially available product with 50% moisture content (5% Pd carbon powder with 50.0% moisture content, E-type, pH 6.0, manufactured by N. E. Chemcat Corp.) at room temperature for one day under a reduced pressure using a vacuum pump. The temperature of the autoclave was raised with stirring the mixture under a hydrogen pressure of 20 kg/cm$^2$. Then the mixture was kept for 10 hours under a hydrogen pressure of 200 kg/cm$^2$ at 190° C. The hydroxyl value at the completion of the reaction was 366.9 [theoretical value: 387.25 (as an ether alcohol with an average alkyl substituent number of 3.0)]. The reaction mixture was dissolved in 200 ml of hexane, and the mixture was subjected to a pressure-filtration through a membrane filter (PTFE, 0.2 μm). The filtrate was evaporated to give 482.73 g of hydrogenated Compound (13b) (yield: 77.8%). The composition of the hydrogenated compound determined by gas chromatography was as follows: 21% of dialkyl ether; 20% of trialkyl ether; 37% of dialkyl ether monoketal; and 8% of trialkyl ether monoketal. 360 g of the compound was purified by silica gel column chromatography using a hexane/ethanol (vol/vol=97/3) developing solvent to give 66.0 g of Compound (13b). The purity of the obtained Compound (13b) as determined by gas chromatography was 98.3%, and the hydroxyl value was 267 (theoretical value: 259).

IR (NEAT, cm$^{-1}$):
3436 (O—H stretching), 2960, 2878 (C—H stretching), 1470, 1377 (C—H deformation), 1092 (C—O stretching)

$^1$H NMR (CDCl$_3$, δ ppm):
0.80–1.09 (18H, multiplet, —CH(C$\underline{H}_3$)$_2$)
0.80–1.30 (9H, multiplet, —OCH(C$\underline{H}_3$)CH$_2$—, (—O—)$_2$C(C$\underline{H}_3$)CH$_2$—)
1.30–1.65 (8H, multiplet, —C$\underline{H}_2$CH(CH$_3$)$_2$)
1.65–1.82 (2H, multiplet, —C$\underline{H}$(CH$_3$)$_2$)
2.36–2.82 (2H, broad singlet, —O$\underline{H}$)
3.33–4.40 (10H, multiplet, —C$\underline{H}$OC$\underline{H}_2$—, —C$\underline{H}$—O—)

MASS (FD):433 (M+1)

Example 1-14

Synthesis of 1,6-di-O-(1,3-dimethylbutyl)sorbitol [Compound (14)]

The hydrogenated compound obtained in Example 1-13 was purified by further carrying out silica gel column chromatography. That is, after Compound (13b) was eluted with hexane/ethanol (vol/vol=97/3), Compound (14) was eluted with a hexane/ethanol (vol/vol=95/5) developing solvent. As a result, 57.9 g of Compound (14) was obtained. The purity of Compound (14) was determined to be 83.7% by gas chromatography, and the hydroxyl value of the compound was 614 (theoretical value: 641).

IR (NEAT, cm$^{-1}$):
3436 (O—H stretching), 2962, 2873 (C—H stretching), 1470, 1377 (C—H deformation), 1089 (C—O stretching)

$^1$H NMR (CDCl$_3$, δ ppm):
0.85–1.02 (12H, multiplet, —CH(C$\underline{H}_3$)$_3$)
1.15 (6H, doublet, —OCH(C$\underline{H}_3$)—)
1.22–1.64 (4H, multiplet, —C$\underline{H}_2$CH(CH$_3$)$_2$)
1.64–1.90 (2H, multiplet, —C$\underline{H}$(CH$_3$)$_2$)
3.32 (4H, singlet, —O$\underline{H}$)
3.45–4.02 (10H, multiplet, —C$\underline{H}$OC$\underline{H}_2$—, —C$\underline{H}$—O—)
MASS (FD):351 (M+1)

Example 1-15

Synthesis of 1,6-di-O-(1,3-dimethylbutyl)-di-O-methyl-O-(1,3-dimethylbutylidene)sorbitol [Compound (15)]

In a 1-liter reaction vessel equipped with a thermometer, a reflux condenser, a dropping funnel, and a stirrer, 15.6 g (0.39 mol) of sodium hydride (content:60%, oily) was placed. The sodium hydride was washed with 100 ml of hexane by decantation. To the vessel, 200 ml of toluene was added and stirred, to which 64.1 g (0.15 mol) of Compound (13b) obtained in Example 1-13 dissolved in 100 ml of toluene was added dropwise over 15 minutes at room temperature. The mixture was further stirred for 1 hour at 100° C. After the mixture was cooled to 40° C., 49.1 g (0.39 mol) of dimethyl sulfate was added dropwise over 1 hour with the temperature maintained below 60° C. After the mixture was further stirred for 1 hour at 60° C. and cooled, 156 g of 10% aqueous solution (0.39 mol) of sodium hydroxide was added and the mixture was stirred at 70° to 80° C. for 1 hour. After cooling, the mixture was allowed to phase separate. The water layer was extracted twice with 150 ml of diethyl ether, and the organic layer was combined with ether extracts. The mixture was washed three times with 100 ml of saturated brine, dried over anhydrous sodium sulfate, and evaporated to distill away the solvent to give 68.0 g of viscous oily substance. The substance obtained was purified by silica gel column chromatography using a hexane/diethyl ether [95/5–90/10 (vol/vol)] developing solvent. As a result, 56.6 g of Compound (15) was obtained, The purity determined by gas chromatography was 97.7%.

IR (NEAT, cm$^{-1}$):
2956, 2878 (C—H stretching), 1470, 1374 (C—H deformation), 1125, 1095 (C—O stretching)

$^1$H NMR (CDCl$_3$, δ ppm):
0.70–1.08 (18H, —CH$_2$CH(C$\underline{H}_3$)$_2$)
1.08–1.30 (9H, —OCH(C$\underline{H}_3$)CH$_2$—, (—O—)$_2$C(C$\underline{H}_3$)CH$_2$—)
1.30–1.67 (6H, —OCH(CH$_3$)C$\underline{H}_2$—, (—O—)$_2$C(CH$_3$)C$\underline{H}_2$—) 1.67–1.96 (3H, —C$\underline{H}$(CH$_3$)$_2$) 3.22–4.25 (16H, —O—C$\underline{H}_2$—, —O—C$\underline{H}$—, —OC$\underline{H}_3$)

Example 1-16

Synthesis of a mixture of 2,3,4,5-tetra-O-methyl-1,6-di-O-(1,3-dimethylbutyl)sorbitol, 2,4,5-tri-O-methyl-1,3,6-tri-O-(1,3-dimethylbutyl)sorbitol, 1,6-di-O-(1,3-dimethylbutyl)-di-O-methyl-O-(1,3-dimethylbutylidene)sorbitol, O-methyl-1,3,6-tri-O-(1,3-dimethylbutyl)-O-(1,3-dimethylbutylidene)sorbitol, 2,3,4,5,6-penta-O-methyl-1-O-(1,3-dimethylbutyl)sorbitol, and di-O-methyl-1,3,6,x-tetra-O-(1,3-dimethylbutyl)sorbitol [Compounds (16c)]

1) Ketals formed from sorbitol and methyl isobutyl ketone: Compounds (16a)

In a 3-liter reaction vessel equipped with a thermometer, a reflux condenser, a Dean and Stark trap, a calcium chloride tube, and a stirrer, 363.76 g (1.997 mol) of D-sorbitol, 1200 g (11.981 mol) of methyl isobutyl ketone, 18.99 g (0.0998 mol) of p-toluene sulfonic acid 1 hydrate, and 300 ml of hexane were placed and heated with stirring. A reaction was carried out at a temperature of from 93° to 95° C. for 5 hours while distilling off 60% of a predetermined amount of water. After being cooled to 60° C., the reaction mixture was neutralized by adding 21.16 g (0.1996 mol) of sodium carbonate, and stirred at 60° C. for 30 minutes. After 200 g of water was added to the mixture and stirred at 60° C. for 30 minutes, the mixture was allowed to stand to separate into two layers. After the lower layer was discarded, the remaining mixture was washed with 200 g of saturated brine, and evaporated to give 544.6 g of crude Compounds (16a). The obtained crude Compounds (16a) was subjected to a reduced-pressure distillation and a forerun was discarded. 486.2 of the residue obtained was subjected to an adsorption treatment by passing through 24.31 g (5% by weight to the residue) of activated clay on a filter (PTFE, 0.2 μm) under pressure. As a result, 471.3 g of Compounds (16a) was obtained (yield: 55.1%). The purity of Compounds (16a) as determined by gas chromatography was 95% [including both diketal and triketal; diketal/triketal=33/67 (weight ratio)].

2) Hydrogenated compounds of ketals formed from sorbitol and methyl isobutyl ketone: Compounds (16b)

In a 1-liter autoclave, 450 g (1.120 mol) of Compounds (16a) obtained above, which was sufficiently dehydrated, and 9.0 g (2% by weight) of 5% Pd/C catalyst were placed, the 5% Pd/C catalyst being prepared by drying a commercially available product with 50% moisture content (5% Pd carbon powder with 50.0% moisture content, E-type, pH 6.0, manufactured by N. E. Chemcat Corp.) at room temperature for one day under a reduced pressure using a vacuum pump. The temperature of the autoclave was raised with stirring the mixture under a hydrogen pressure of 20 kg/cm$^2$. Then the mixture was kept for 20 hours under a hydrogen pressure of 200 kg/cm$^2$ at 190° C. After the completion of the reaction, the mixture was dissolved in 200 ml of hexane, and subjected to a pressure-filtration through a membrane filter (PTFE, 0.2 μm). Hexane in the filtrate was distilled away to give 433 g of a crude Compounds (16b) (yield of the crude compounds: 95%).

The purity of the compounds obtained was determined to be 90% by gas chromatography (including dialkyl ether, trialkyl ether, dialkyl ether monoketal, trialkyl ether monoketal, monoalkyl ether, and tetraalkyl ether; weight ratio of the components: dialkyl ether:trialkyl ether:dialkyl ether monoketal:trialkyl ether monoketal:monoalkyl ether:tetraalkyl ether=63.5:16.0:14.7 2.9:2.7:0.2; hydroxyl value=444.5).

3) A mixture of 2,3,4,5-tetra-O-methyl-1,6-di-O-(1,3-dimethylbutyl)sorbitol, 2,4,5-tri-O-methyl-1,3,6-tri-O-(1,3-dimethylbutyl)sorbitol, 1,6-di-O-(1,3-dimethylbutyl)-di-O-methyl-O-(1,3-dimethylbutylidene)sorbitol, 1,6,x-tri-O-(1,3-dimethylbutyl)-O-methyl-O-(1,3-dimethylbutylidene)sorbitol, 2,3,4,5,6-penta-O-methyl-1-O-(1,3-dimethylbutyl)sorbitol, and di-O-methyl-1,3,6,x-tetra-O-(1,3-dimethylbutyl)sorbitol: Compounds (16c)

In a 2-liter reaction vessel equipped with a thermometer, a reflux condenser, a dropping funnel, and a stirrer, 28.5 g (1.19 mol) of sodium hydride powder and 900 ml of toluene were placed. 100 g (0.79 mol as hydroxyl group) of Compounds (16b) obtained in 2) above was dissolved in 100 ml of toluene, and added dropwise to the vessel over 30 minutes with stirring under nitrogen atmosphere. Then 50 ml of toluene was added to the vessel. The reaction mixture was heated to 110° C. and refluxed with stirring for 1 hour at 110° C. After the mixture was cooled to 50° C., 149.9 g (1.19 mol) of dimethyl sulfate was added dropwise over 1 hour with the temperature maintained at 50° C. 300 ml of toluene was added and the mixture was matured for 1 hour at 80° C. After the mixture was cooled and 476 g of 10% aqueous solution (1.19 mol) of sodium hydroxide was added, the mixture was stirred at 70° to 80° C. for 30 minutes. The mixture was cooled to room temperature and allowed to stand to phase separate. The lower layer was discarded. The upper toluene layer was washed 4 times with saturated brine, dried over anhydrous sodium sulfate, and evaporated to give 98.4 g of viscous oily substance, Compounds (16c) (yield: 89%). The purity of the substance was determined to be 90% by gas chromatography. The composition of the substance was as follows: 56.8% by weight of 2,3,4,5-tetra-O-methyl-1,6-di-O-(1,3-dimethylbutyl)sorbitol, 14.3% by weight of 2,4,5-tri-O-methyl-1,3,6-tri-O-(1,3-dimethylbutyl)sorbitol, 3.2% by weight of 1,6-di-O-(1,3-dimethylbutyl)-di-O-methyl-O-(1,3-dimethylbutylidene)sorbitol, 2.6% by weight of 1,3,6-tri-O-(1,3-dimethylbutyl)-O-methyl-O-(1,3-dimethylbutylidene)sorbitol, 2.4% by weight of 2,3,4,5,6-penta-O-methyl-1-O-(1,3-dimethylbutyl)sorbitol, and 2% by weight of di-O-methyl-1,3,6,x-tetra-O-(1,3-dimethylbutyl)sorbitol IR (NEAT, cm$^{-1}$):
2956, 2878, 2830 (C—H stretching), 1470, 1374, 1350 (C—H deformation), 1110 (C—O stretching)

Example 2-1

With respect to each of the oils used in the present inventive products and comparative products, kinematic viscosities at 40° C. and 100° C. were measured in accordance with JIS K-2283. The results are shown in Tables 1 and 2.

TABLE 1

| No. of Oil for Inventive Product | Compound Structure | Kinematic Viscosity (mm$^2$/s) 40° C. | 100° C. | Fluidity at Low Temperature |
|---|---|---|---|---|
| (6) | 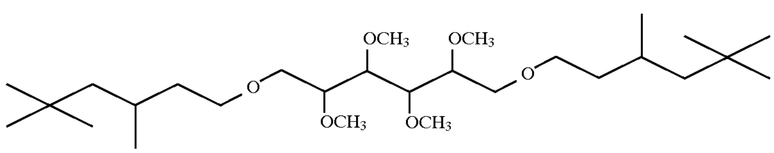 | 27.03 | 4.62 | Fluid |
| (7) | 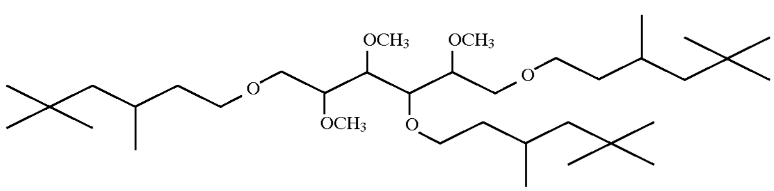 | 56.61 | 7.20 | Fluid |
| (15) | | 16.37 | 3.16 | Fluid | m + n = 2
(Ether alkyl groups, except for those at both ends, may be arranged at random or in block form.)

Note: The parenthesized figures correspond to the numbers for oils in Examples 1-1 to 1-16.

TABLE 2

| No. of Oil for Inventive Product | Compound Structure | Kinematic Viscosity (mm²/s) 40° C. | 100° C. | Fluidity at Low Temperature |
|---|---|---|---|---|
| (11) | 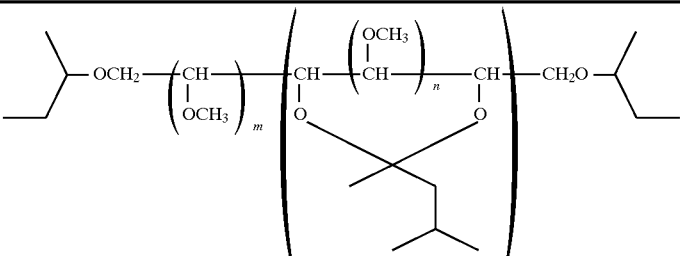 m + n = 2 (Ether alkyl groups, except for those at both ends, may be arranged at random or in block form.) | 11.55 | 2.39 | Fluid |
| (12) | 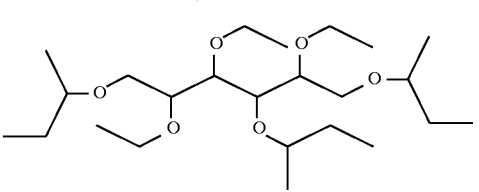 | 11.73 | 2.61 | Fluid |
| (M-1) | (6) 67% by weight + (7) 33% by weight | 35.29 | 5.37 | Fluid |
| (8-1) | Synthesized according to Example 1-8-1. | 24.36 | 4.20 | Fluid |
| (8-2) | Synthesized according to Example 1-8-2. | 45.41 | 6.22 | Fluid |
| (16c) | Synthesized according to Example 1-16. | 11.94 | 2.62 | Fluid |
| Oil (1) for Comparative Product | Naphthene oil | 30.0 | 4.4 | Fluid |

Example 2-2

With respect to each of the oils used in the present inventive products and comparative products, fluidity at low temperatures was measured. Specifically, oil samples used in Example 2-1 were placed in a constant temperature vessel maintained at −20° C. for 1 hour, and observed whether or not the samples showed fluidity. The results are shown in Tables 1 and 2.

Example 2-3

Each of inventive products and comparative products was prepared, each being a composition consisting of 1,1,1,2-tetrafluoroethane (HFC134a) and one of the oils for inventive and comparative products listed in Tables 3 and 4, and the compatibility between the hydrofluorocarbon and the oil was evaluated. Specifically, the two-phase separation temperature for 1,1,1,2-tetrafluoroethane at low temperatures was measured at sample oil concentrations of 10 vol %, 20 vol %, 30 vol %, and 40 vol %. The results are shown in Tables 3 and 4.

As is evident from Tables 3 and 4, the oils used in the inventive products had a better compatibility with HFC134a than those used in the comparative products.

TABLE 3

| No. of Oil for Inventive Product | Compound Structure | Separation Temperature at Low Temperature (°C.) | | | |
|---|---|---|---|---|---|
| | | 10 vol % | 20 vol % | 30 vol % | 40 vol % |
| (6) | 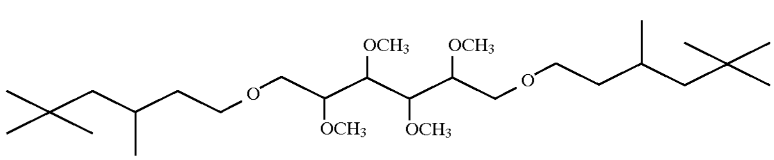 | −56 | −52 | −51 | −52 |

TABLE 3-continued

| No. of Oil for Inventive Product | Compound Structure | Separation Temperature at Low Temperature (°C.) | | | |
|---|---|---|---|---|---|
| | | 10 vol % | 20 vol % | 30 vol % | 40 vol % |
| (15) | 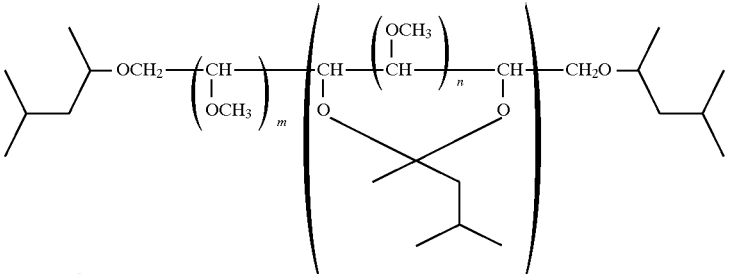 m + n = 2 (Ether alkyl groups, except for those at boty ends, may be arranged at random or in block form.) | −48 | −39 | −34 | −39 |
| (11) | 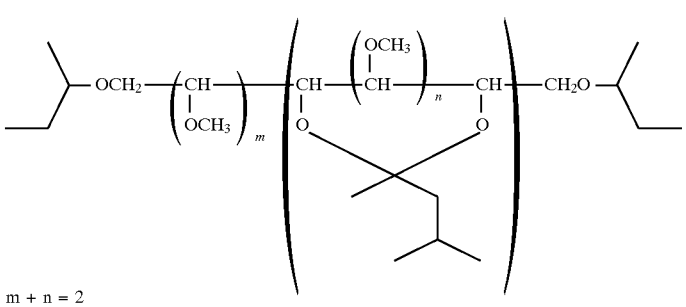 m + n = 2 (Ether alkyl groups, except for those at both ends, may be arranged at random or in block form.) | <−70 | <−70 | <−70 | <−70 |

TABLE 4

| No. of Oil for Inventive Product | Compound Structure | Separation Temperature at Low Temperature (°C.) | | | |
|---|---|---|---|---|---|
| | | 10 vol % | 20 vol % | 30 vol % | 40 vol % |
| (12) | 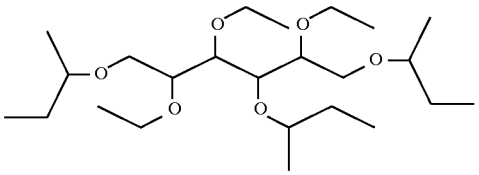 | <−70 | <−70 | −69 | <−70 |
| M-1 | (6) 67% by weight + (7) 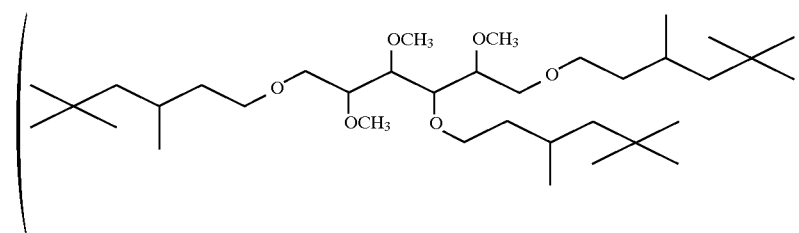 33% by weight | −18 | −12 | −16 | −26 |
| (16c) Oil (1) for Comparative Product | Synthesized according to Example 1-16. Naphthene oil | <−70 >20 | <−70 >20 | <−70 >20 | <−70 >20 |

Example 2-4

Each of the present inventive products was tested for the thermal stability by a sealed tube test.

Specifically, 10 g of an oil with a moisture content adjusted below 20 ppm and 5 g of HFC134a were placed in a glass tube. After iron, copper, and aluminum were added thereto as catalysts, the glass tube was sealed. After tested at 175° C. for 14 days and 28 days, the composition of oil and HFC134a was observed for its appearance and presence of precipitation. After HFC134a was removed, the acid value of oil was measured. The results are shown in Tables 5 and 6.

As is evident from Tables 5 and 6, the thermal stability of the inventive products was good, all of the inventive products showing no abnormality in appearance, and no precipitation.

Example 2-5

Each of the present inventive products and a comparative product were tested for the hydrolysis resistance by a sealed tube test.

Specifically, 10 g of an oil with a moisture content adjusted at 3000 ppm, and 5 g of HFC134a were placed in a glass tube. After iron, copper, and aluminum were added thereto as catalysts, the glass tube was sealed. After tested at 175° C. for 14 days, the composition of oil and HFC134a was observed for its appearance and presence of precipitation. After the hydrofluorocarbon was removed, the acid value of oil was measured. The results are shown in Tables 7 and 8. As is evident from Tables 7 and 8, the hydrolysis resistance of the inventive products was good, with showing no abnormality in appearance, no precipitation, and, unlike the comparative product using an ester, no increase in the acid value.

TABLE 5

| No. of Oil for Inventive Product | Compound Structure | Test Period | Appearance | Precipitation | Acid Value (mgKOH/g) Before Test | Acid Value (mgKOH/g) After Test |
|---|---|---|---|---|---|---|
| (11) | [structure; $m + n = 2$; (Ether alkyl groups, except for those at both ends, may be arranged at random or in block form.)] | 14 days | Normal | None | <0.05 | <0.05 |
| | | 28 days | Normal | None | <0.05 | <0.05 |
| (12) | [structure] | 14 days | Normal | None | <0.05 | <0.05 |
| | | 28 days | Normal | None | <0.05 | <0.05 |

TABLE 6

| No. of Oil for Inventive Product | Compound Structure | Test Period | Appearance | Precipitation | Acid Value (mgKOH/g) Before Test | Acid Value (mgKOH/g) After Test |
|---|---|---|---|---|---|---|
| (8-2) | Synthesized according to Example 1-8-2. | 14 days | Normal | None | <0.05 | <0.05 |
| | | 28 days | Normal | None | <0.05 | <0.05 |
| (16c) | Synthesized according to Example 1-16. | 14 days | Normal | None | <0.05 | <0.05 |
| | | 28 days | Normal | None | <0.05 | <0.05 |

TABLE 7

| No. of Oil for Inventive Product | Compound Structure | Appearance | Precipitation | Sealed Tube Test Acid Value (mgKOH/g) Before Test | After Test |
|---|---|---|---|---|---|
| (11) | [structure: –OCH₂–(CH(OCH₃))ₘ–(CH–CH(OCH₃)–)ₙ with neopentyl-like bridge–CH₂O–; m + n = 2 (Ether alkyl groups, except for those at both ends, may be arranged at random or in block form.)] | Normal | None | <0.05 | <0.05 |
| (12) | [structure: cyclic ether compound] | Normal | None | <0.05 | <0.05 |

TABLE 8

| No. of Oil for Inventive Product | Compound Structure | Appearance | Precipitation | Sealed Tube Test Acid Value (mgKOH/g) Before Test | After Test |
|---|---|---|---|---|---|
| (8-2) | Synthesized according to Example 1-8-2. | Normal | None | <0.05 | <0.05 |
| (16c) | Synthesized according to Example 1-16. | Normal | None | <0.05 | <0.05 |
| Oil (2) for Comparative Product | Trimethylolpropane tricaproate. | Normal | None | 0.05 | 7.3 |

Example 2-6

With respect to each of the oils used in the present inventive products and comparative products, volume resistivity at 25° C. was measured in accordance with JIS C-2101. The results are shown in Tables 9 and 10.

As is evident from Tables 9 and 10, the oils used in the inventive products had better volume resistivity than those used in the comparative products.

TABLE 9

| No. of Oil for Inventive Product | Compound Structure | Volume Resistivity ($\Omega \cdot cm$) |
|---|---|---|
| (15) | 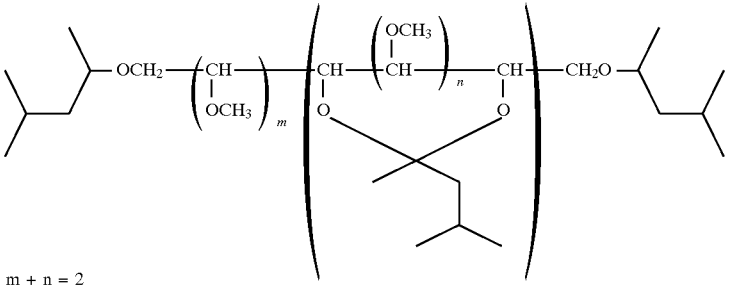<br>m + n = 2<br>(Ether alkyl groups, except for those at both ends, may be arranged at random or in block form.) | $2.0 \times 10^{14}$ |
| (11) | 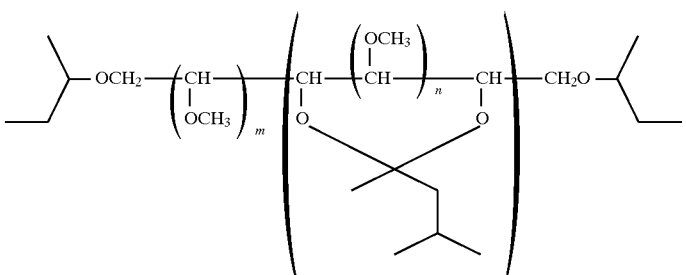<br>m + n = 2<br>(Ether alkyl groups, except for those at both ends, may be arranged at random or in block form.) | $2.1 \times 10^{12}$ |
| (12) | 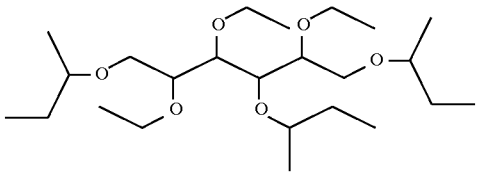 | $2.0 \times 10^{13}$ |

TABLE 10

| No. of Oil for Inventive Product | Compound Structure | Volume Resistivity ($\Omega \cdot cm$) |
|---|---|---|
| (8-2) | Synthesized according to Example 1-8-2. | $9.9 \times 10^{13}$ |
| (16c) | Synthesized according to Example 1-16. | $9.4 \times 10^{13}$ |
| Oil (3) for Comparative Product | $CH_3$<br>$\vert$<br>$CH_3O(BO)aCH_2CH_2CHO(BO)bCH_3$<br>(a + b = 15) | $2.0 \times 10^{11}$ |
| Oil (4) for Comparative Product | Unirube MB-11 ($\overline{MW}$1000)<br>(Polyoxypropylene glycol monobutyl ether) | $5.0 \times 10^{9}$ |
| Oil (5) for Comparative Product | Propyleneoxide-1,2-epoxybutane copolymer with methyl ethers at both ends ($\overline{MW}$1245) | $1.3 \times 10^{10}$ |

Example 2-7

Each of the present inventive products, each comprising a hydrofluorocarbon and a refrigeration oil containing an ether compound used in the present invention and additives, was tested for the thermal stability, etc. by a sealed tube test.

Specifically, 10 g of an oil with a moisture content adjusted at 3000 ppm and 5 g of HFC134a were placed in a glass tube. After iron, copper, and aluminum were added thereto as catalysts, the glass tube was sealed. After tested at 175° C. for 14 days, the composition of oil and HFC134a was observed for its appearance and presence of precipitation. After HFC134a was removed, the moisture content of the oil was measured. The results are shown in Table 11. As is evident from Table 11, the thermal stability of the inventive products was good, with all of the inventive products showing no abnormality in appearance, and no precipitation. Also, a good dehydration could be achieved.

While the invention has been described in detail and with reference to specific embodiments thereof, it will be apparent to one skilled in the art that various changes and modifications can be made therein without departing from the spirit and scope thereof.

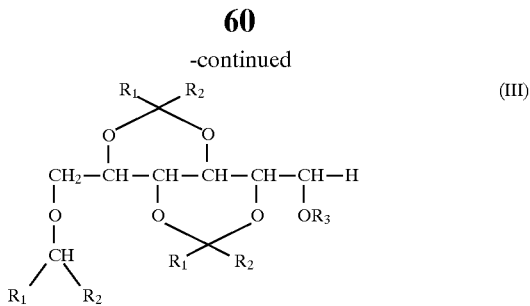

(III)

TABLE 11

| Inventive Product | Ether Used in the Present Invention | Additives (Amount[*1]) | Appearance | Precipitation | Water Content (ppm) Before Test | Water Content (ppm) After Test |
|---|---|---|---|---|---|---|
| A-1 | (8-2) Synthesized according to Example 1-8-2. | 1,3-dicyclohexylcarbodiimide (3) | Normal | None | 3000 | 212 |
| A-2 | (15) | 1,3-dicyclohexylcarbodiimide (3) | Normal | None | 3000 | 198 |
| A-3 | (6) | 1,1-bis(2-methylpropoxy)-cyclohexane (3) | Normal | None | 3000 | 154 |
| A-4 | (6) | Glycidyl 2-ethylhexanoate (3) | Normal | None | 3000 | 645 |
| A-5 | (12) | 3,4-epoxycyclohexylmethyl 3,4-epoxycyclohexanecarboxylate (3) | Normal | None | 3000 | 312 |

[*1]: Parts by weight based on 100 parts by weight of the ether used in the present invention.

What is claimed is:

1. A polyol ether derivative represented by any one of the following general formulas (I) to (IV):

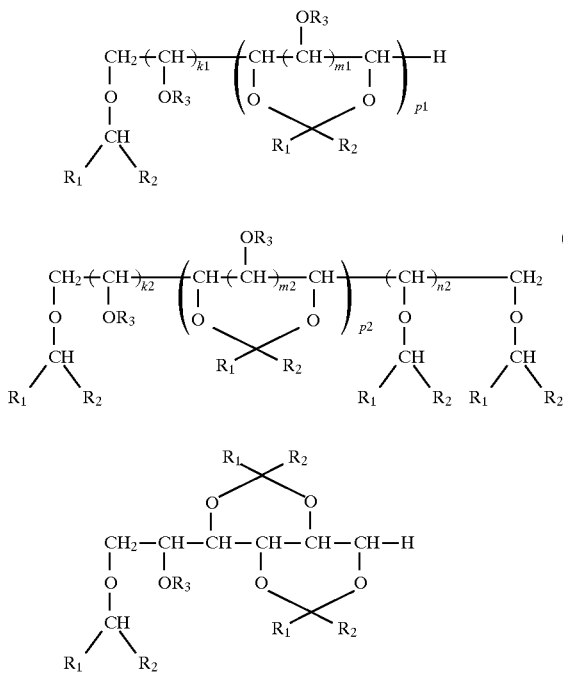

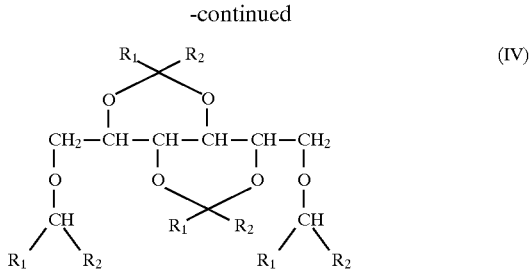

(IV)

wherein $R_1$ represents a hydrogen atom, a linear alkyl group having 1–21 carbon atoms or a branched alkyl group having 3–21 carbon atoms; $R_2$ represents a branched alkyl group having 3–17 carbon atoms when $R_1$ represents a hydrogen atom, or $R_2$ represents a linear alkyl group having 1–21 carbon atoms or a branched alkyl group having 3–21 carbon atoms when $R_1$ represents a linear alkyl group having 1–21 carbon atoms or a branched alkyl group having 3–21 carbon atoms; $R_1$ and $R_2$ may together join to form a ring with an alkylene group having 2–13 carbon atoms; 2 to 6 pairs of $R_1$ and $R_2$ may be identical or different; $k_1$ represents a number of 0–5, $p_1$ represents a number of 0–2, $m_1$ represents 0 or 1, wherein $k_1$, $p_1$ and $m_1$ satisfy the equation $k_1+(m_1+2)p_1=5$; $k_2$ and $n_2$ each represents a number of 0–4, $p_2$ represents a number of 0–2, $m_2$ represents 0 or 1, wherein $k_2$, $p_2$, $m_2$ and $n_2$ satisfy the equation $k_2+(m_2+2)p_2+n_2=4$; $R_3$ represents a hydrogen atom, a linear alkyl group having 1–8 carbon atoms or a branched alkyl group having 3–8 carbon atoms; and repeating units in formulas (I) and (II) may be arranged at random or in block form.

2. The polyol ether derivative according to claim 1, wherein an alcohol residue of the polyol ether derivative is derived from sorbitol.

* * * * *